United States Patent [19]

Nagasaki et al.

[11] Patent Number: 4,622,584
[45] Date of Patent: Nov. 11, 1986

[54] AUTOMATIC DIMMER FOR ENDOSCOPE

[75] Inventors: Tatsuo Nagasaki, Musashino; Hiroyoshi Fujimori, Hachioji, both of Japan

[73] Assignee: Olympus Optical Co., Ltd., Tokyo, Japan

[21] Appl. No.: 647,515

[22] Filed: Sep. 5, 1984

[30] Foreign Application Priority Data

Sep. 5, 1983 [JP] Japan ............................ 58-163585
Sep. 5, 1983 [JP] Japan ............................ 58-163590
Sep. 5, 1983 [JP] Japan ............................ 58-163595
Sep. 5, 1983 [JP] Japan ............................ 58-163599
Oct. 3, 1983 [JP] Japan ............................ 58-184691
Oct. 3, 1983 [JP] Japan ............................ 58-184692

[51] Int. Cl.⁴ .......................... A61B 1/04; A61B 1/06; H04N 5/235; H04N 11/06
[52] U.S. Cl. ........................................ 358/98; 128/6; 358/42; 358/44; 358/168
[58] Field of Search ..................... 358/98, 168, 41, 42, 358/44; 128/6-9; 350/96.26; 356/241

[56] References Cited

U.S. PATENT DOCUMENTS 3,774,173 11/1973 Love ................................ 350/96.27
4,527,552 7/1985 Hattori ................................ 128/6
4,532,918 8/1985 Wheeler ............................... 128/6

FOREIGN PATENT DOCUMENTS 0039458 11/1981 European Pat. Off. ............... 128/6

Primary Examiner—Howard W. Britton
Attorney, Agent, or Firm—Armstrong, Nikaido, Marmelstein & Kubovcik

[57] ABSTRACT

Automatic dimmer for endoscope to automatically set to a proper value the quantity of light to irradiated to a subject or the quantity of light reflected from the subject to the solid pickup element. This equipment forms the dimmer signal on basis of the signal level output from the solid pickup element and controls the quantity of light passed on the light quantity changing member provided on the path of illuminating light irradiated from the light source to the subject or on the path of the light received by the solid pickup element.

20 Claims, 30 Drawing Figures

FIG. 8
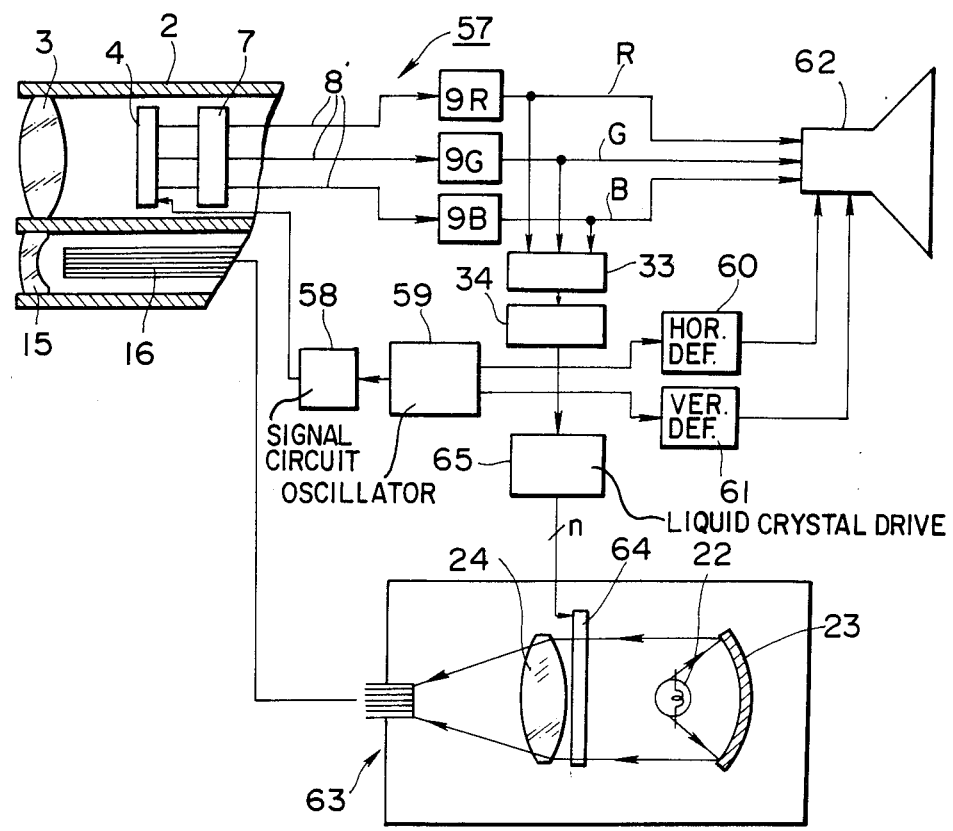
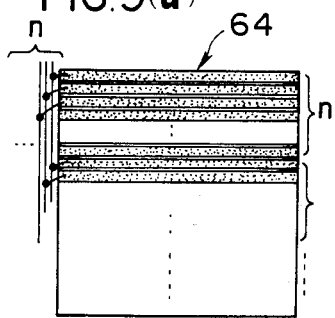
FIG.9(a)
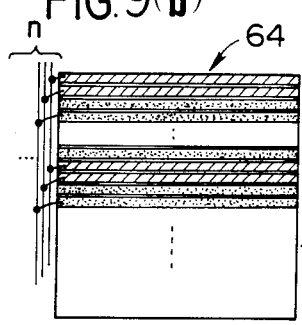
FIG.9(b)
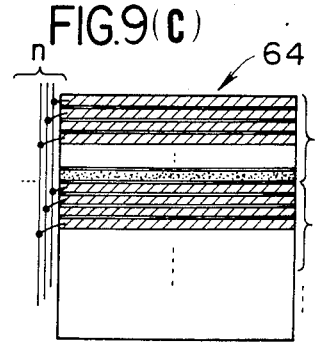
FIG.9(c)

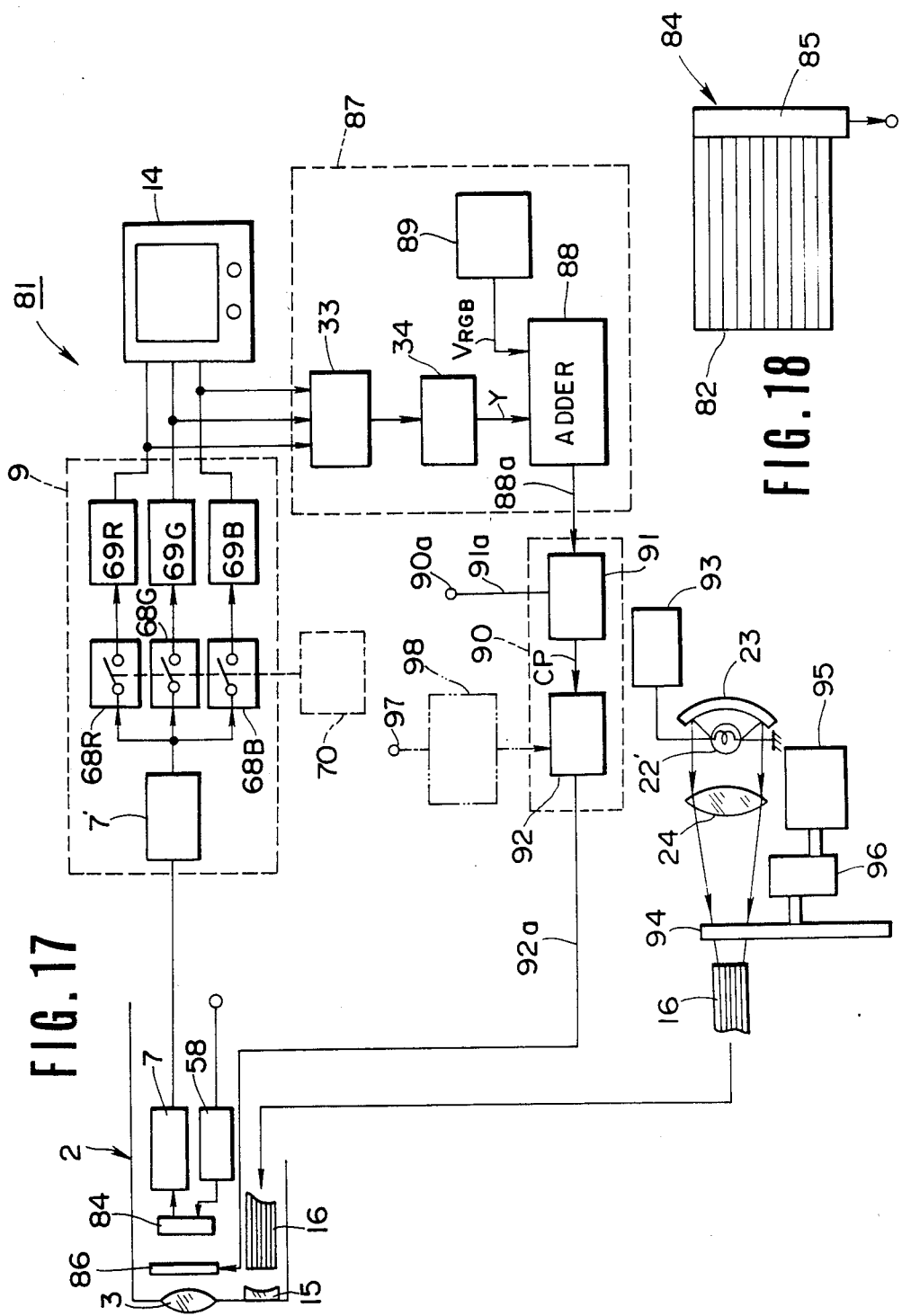

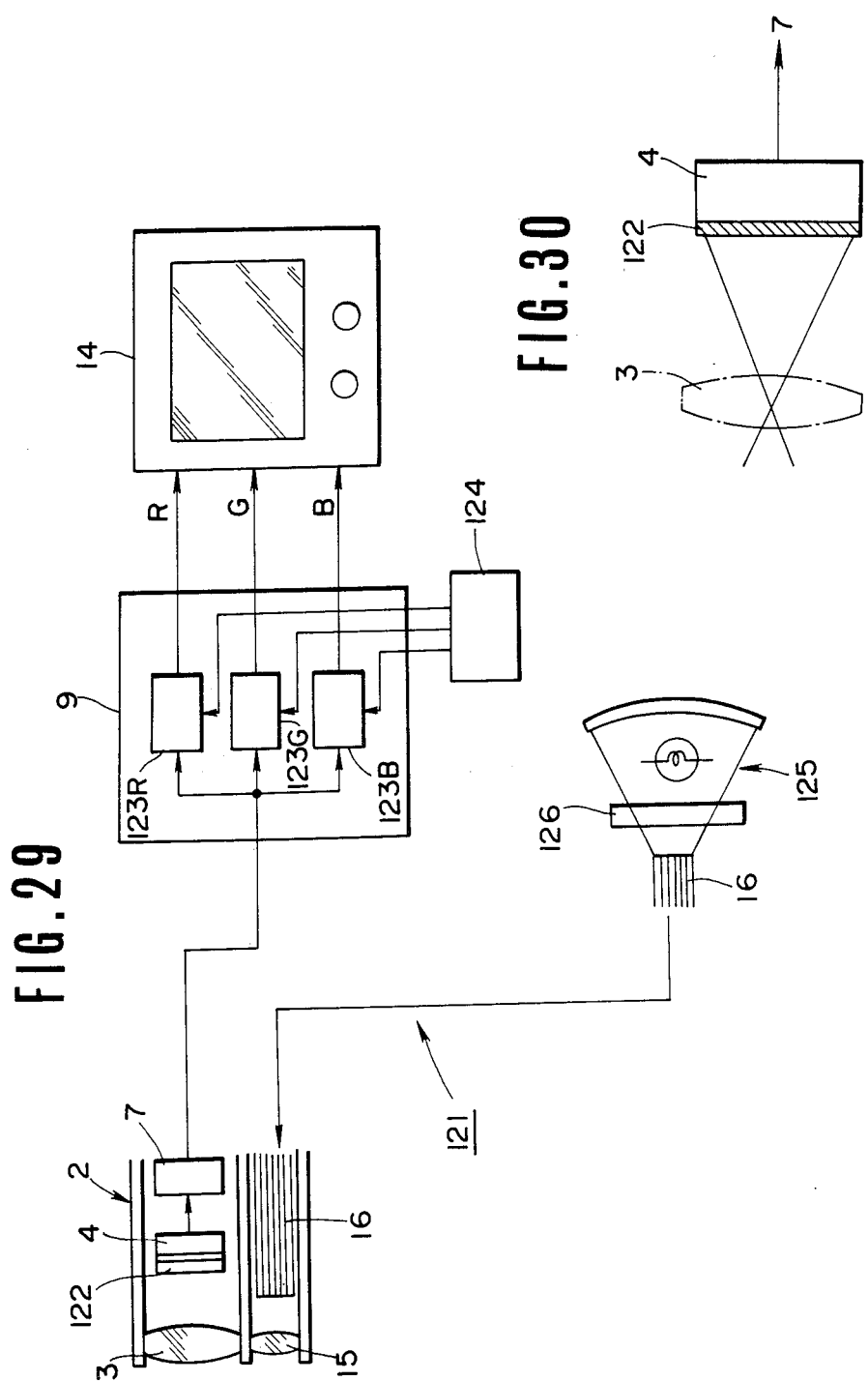

AUTOMATIC DIMMER FOR ENDOSCOPE

BACKGROUND OF THE INVENTION

This invention concerns an automatic dimmer which can automatically control the quantity of light received to suit the image pickup in an endoscope which uses a solid pickup element as the image pickup means.

Recently the endoscope which uses a solid pickup element and makes it possible to display the picture of a subject on a display device such as CRT is being realized.

In comparison with those which form the optical image on the image guide fibers, the electronic endoscope which uses the above solid pickup element can more easily record the image and has an advantage that it can be made smaller and smaller, as the high integrating technology advances.

But when the solid pickup element is used and if the quantity of light incident upon the light receiving elements on the image pickup face is too big, excess charge leaks in the periphery causing smearing and blooming and making it impossible to reproduce a true image of that portion and the image cannot be picked up until the normal state is recovered.

There are some devices which can mechanically control the strength of the illuminating light on the light source side to prevent the blooming phenomenon, but it is almost impossible to achieve a proper intensity of illumination in a short time because the control must be made in accordance with the distance to the subject when they are used in a human body and also the distance to the inside wall of the body changes in a complicated way when the end side of the inserting member is bent.

And when they are used in a human body, the reflecting strength increases when the affected part is wet with body fluids, and the proper intensity of illumination changes depending on the state of the affected part. To the contrary, if the intensity of illumination is too low, the affected part cannot be picked up clearly and good diagnosis cannot be achieved.

BRIEF SUMMARY OF THE INVENTION

The objective of this invention is to provide an automatic dimmer for endoscope which can prevent the blooming phenomenon.

Another objective of this invention is to provide an automatic dimmer for endoscope which can automatically set to the quantity of light suitable for the image pickup and reproduction.

Still another objective of this invention is to provide an automatic dimmer for endoscope which can quickly set to a proper image pickup state.

Other features and advantages of this invention will be made clear by the following explanation.

BRIEF DESCRIPTION OF THE DRAWINGS

FIGS. 8 and 9a, 9b and 9c concern a sixth embodiment of this invention and FIG. 8 is an explanatory drawing to show the structure of the entire endoscope using the embodiment 6 and FIGS. 9a, 9b and 9c show the liquid crystal filters, 9a ) being an explanatory drawing to show the state with voltage not applied, 9b an explanatory drawing to show the light shielding part when the voltage is applied to 2 electrodes and 9c an explanatory drawing to show the light shielding part when the voltage is applied to many electrodes. FIG. 17 is a block diagram to show an endoscope equipped with an eleventh embodiment of this invention, FIG. 18 is an explanatory drawing to show a solid pickup element of line transfer type used in FIG. 17, FIG. 28 is an explanatory drawing to show the liquid crystal filter in a fifthteenth embodiment of this invention and FIG. 29 is a block diagram to show an endoscope equipped with a sixteenth embodiment of this invention, and FIG. 30 is a side view to show a solid pickup element provided with photochromic glass.

DETAILED DESCRIPTION OF THE EMBODIMENTS

Figure 1:
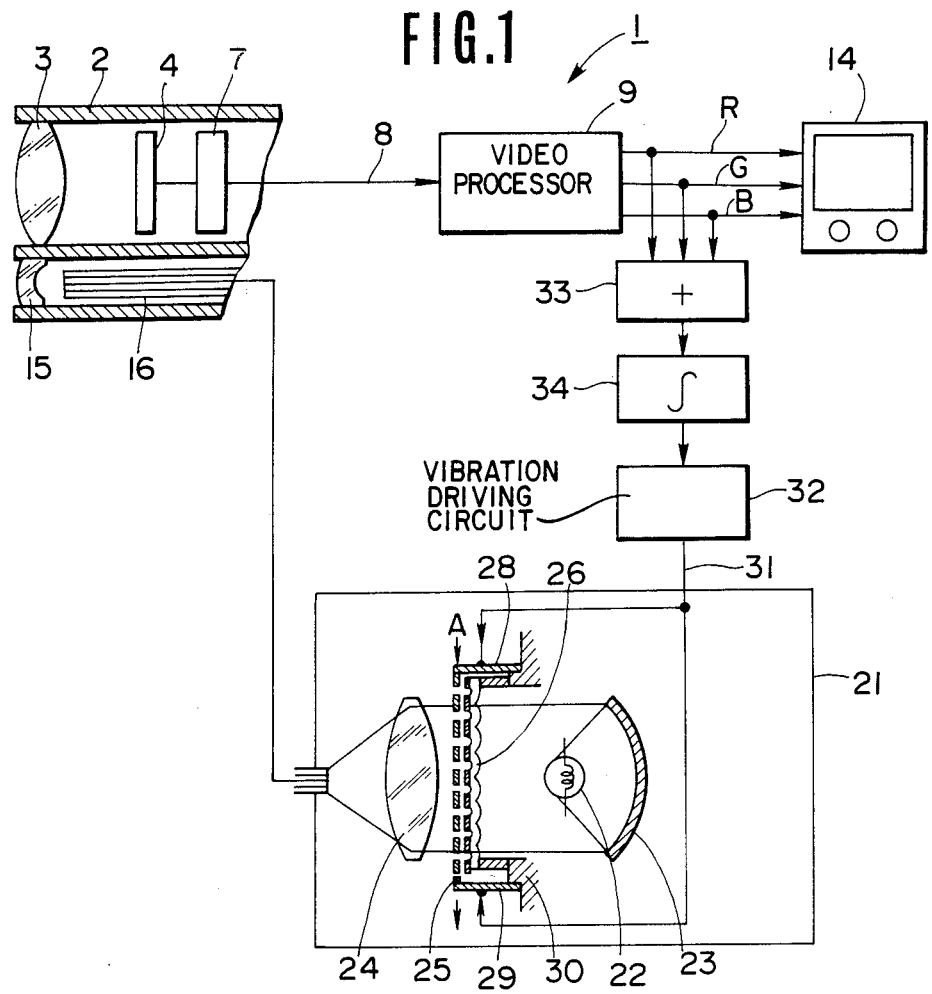
FIGS. 1 and 2 concern the embodiment 1 of this invention and FIG. 1 is an explanatory drawing to show the entire endoscope equipped with the embodiment 1 and FIG. 2 is a schematic cross section to show the enlarged periphery of the light controlling member which controls the quantity of light transmitted in the first embodiment of the invention.

The endoscope 1 equipped with the first embodiment is provided with an object lens 3 for image forming on the end side of the long and narrow inserting member 2 and with a solid pickup element 4 such as CCD (charge coupled device) in such a place that its image pickup face is located at the image forming position of the said object lens 3. On the image pickup face of the solid pickup element 4, many light receiving elements which have photoelectric conversion function are regularly arranged. Before the image pickup face, mosaic type tri-color filters (not illustrated) to transmit only the light of the waveform of 3 primary colors are provided to correspond to the arrangement of the light receiving elements, and in accordance with the clock signal applied to the said solid pickup element 4, the signal to correspond to each picture element passed through the red, green and blue transmission filters is sequentially output, and the said signal is amplified by the preamplifier 7 with low noise factor, passed through the signal cable 8, separated into the color signals R, G and B and taken in by the sample hold circuit in the video processor 9 provided on the hand side of the inserting member 2 and then, after the synchronizing signal is added, input to the monitoring color television set 14 to be displayed as a color picture.

In the aforementioned inserting member 2, a light distributing lens 15 is provided adjacent to the object lens 3 and a light guide 16 is inserted in such a way that its irradiating end faces the inside of the said light distributing lens 15.

The rear end of the said light guide 16 is connected in a removable way to light source equipment 21.

At the rear end, the incident and of the illuminating light, of the light guide 16, the illuminating light from the illuminating lamp 22 is reflected by the reflector 23, condensed by the condenser lens 24 and irradiated.

And a means to control the illuminating light irradiated by the illuminating lamp 22 to the incident end of the light guide 16 is formed as follows.

Figure 2:
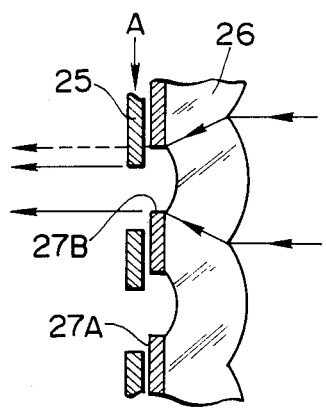

In the light path between the condenser lens 24 and the illuminating lamp 22, for example, at the pupil position of the condenser lens 24, as shown in FIG. 2, reed screen type light shielding plates 25 provided with slit openings and shielding parts and flyeye lens 26 adjacent and corresponding to the said light shielding plates 25 are provided. This flyeye lens 26 consists of many cylindrical lenses.

On the side of this flyeye lens 26 facing the light shielding plates 25, reed screen type shielding part 27A and transmitting part 27B are provided by sticking the light shielding plates similar to the light shielding plates 25 or coating light shielding paint, and the light shielding plates 25 and flyeye lens 26 form a means to change the quantity of light passed.

The flyeye lens 26 refracts at its convex parts the illuminating light of approximately parallel flux coming from the illuminating lamp 22 side, condenses it at the transmitting part 27B of the concave parts on the other side and irradiates it to the light shielding plate 25 side (opening side). This flyeye lens 26 is fixed. The aforementioned means to change the quantity of light passed can be formed with 2 reed-screen-like shielding plates, and in such a case one plate is provided with the flyeye lens 26 to increase the quantity of light which can be utilized for lighting.

Both upper and lower ends of the aforementioned light shielding plate 25 are fixed to the front ends of the bimorph vibrators 28 and 29, the driving means, and the rear ends of the bimorph vibrators 28 and 29 are fixed to the inner wall, etc. of the light source equipment 21 via pedestal 30, etc.

To these bimorph vibrators 28 and 29, control signals for driving are supplied from the bimorph vibrator driving circuit 32 via the lead wire 31. As the level of this driving signal becomes high, the front end side of the bimorph vibrators 28 and 29 moves downward in-phase against the fixed rear end side (shown by arrow A), and with this movement, the light shielding plate 25 also moves downward to reduce the quantity of light passing through the openings of the light shielding plate 25.

The color signals R, G and B output from the aforementioned video processor 9 is also taken in by a dimmer signal forming means and the dimmer signal output from the dimmer signal forming means is added to the aforementioned vibrator driving circuit 32.

This is, to the control input end of the vibrator driving circuit 32, the dimmer signal which is formed by adding the color signals R, G and B output from the video processor 9 with the adder 33 and integrating the illuminance signal with the integrating circuit 34 is applied, and as the dimmer signal level becomes high, the level of the output signal of the vibrator driving circuit 32 becomes high. The above adder 33 is to make the dimmer signal while maintaining the color balance and the integrating circuit 34 is to meet the light receiving period of the signals output from the light receiving elements, and the integrating circuit 34 is set to integral time constant more than about 1 frame, and as the size of the integrated signal level increases, the quantity of the illuminating light coming through the flyeye lens 26 can be decreased by changing from the maximum transmission area where the light can just pass through the openings of the light shielding plate 25.

In the first embodiment thus formed, when the endoscppe 1 is put near to or far from a subject, the quantity of light coming from the subject changes depending on the distance and therefore, the optimum intensity of illumination changes. The signals to correspond to the picture elements output from the solid pickup element 4 in that state are taken in, the color signals R, G and B separated for color display are added and further integrated by the integrating circuit 34, and the vibrator driving circuit 32 is driven by the dimmer signal of the level to reflect the quantity of light reflected from the subject in 1 frame period and the driving control signal is applied to the bimorph vibrators 28 and 29 and the light shielding plate 25 is moved in accordance with the level of the dimmer signal or control signal and a proper intensity of illumination in that state is maintained every time of about 1 frame. Therefore, the operator needs not to adjust the intensity of illumination every time and can concentrate on the diagnosis or medical treatment.

Also, since the intensity of illumination is automatically controlled to a proper value, detailed and accurate diagnosis and proper treatment can be done.

Figure 3:
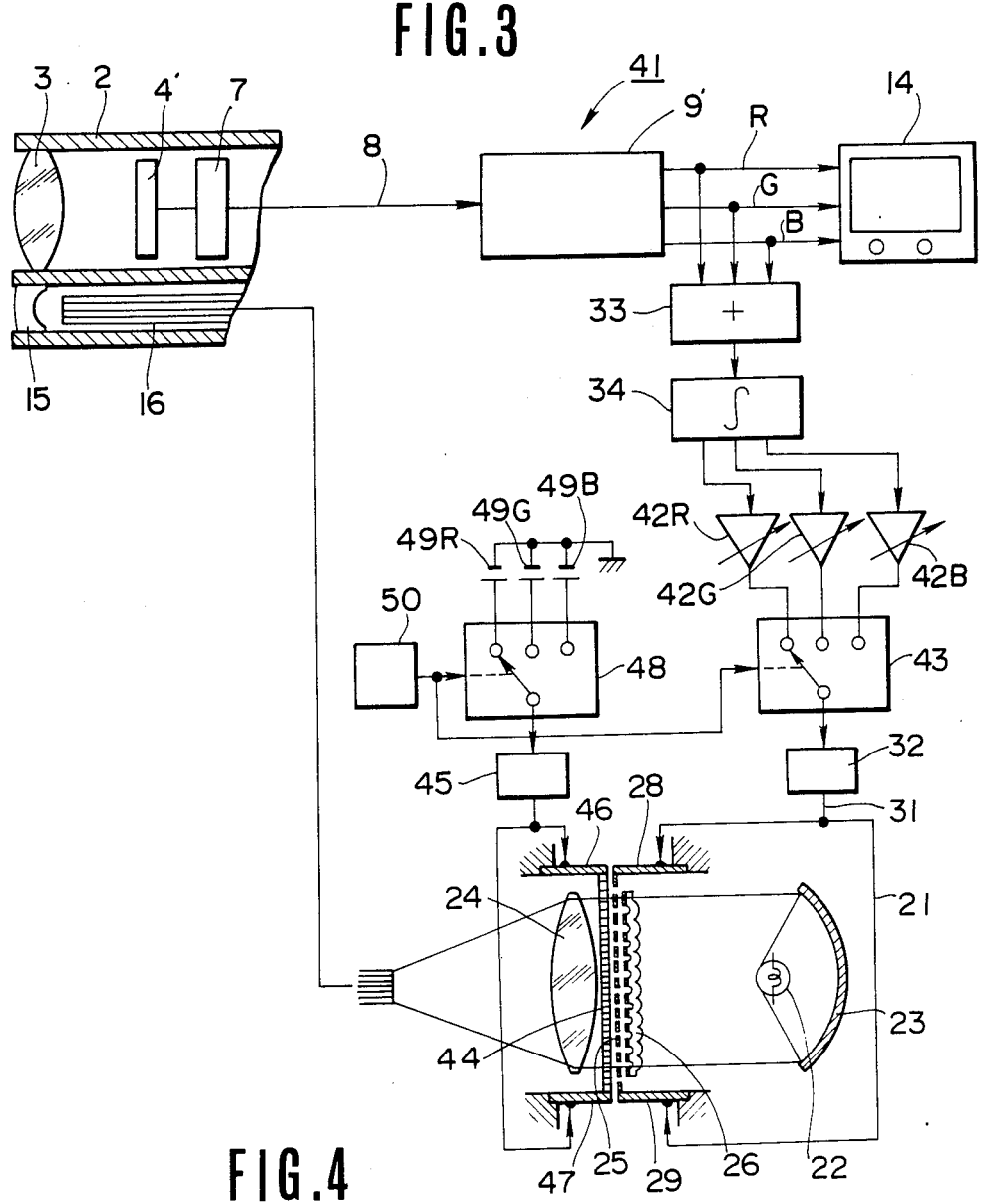
FIGS. 3 and 4 concern a second embodiment of this invention and FIG. 3 is an explanatory drawing to show the entire endoscope equipped with second embodiment and FIG. 4 is a front view to show the structure of the tri-color filter.
Figure 4:
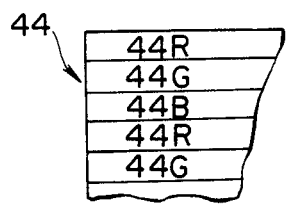

FIG. 3 shows an endoscope equipped with the second embodiment of this invention.

In this second embodiment, the lighting is made in 3 primary colors and the intensity of illumination can be automatically controlled while maintaining the color balance at a proper value.

That is, in the endoscope 41 equipped with the embodiment 2, the color signals R, G and B output via the video processor 9' pass the adder 33 and integrating circuit 34 and are amplified by the semi-fixed amplifiers 42R, 42G and 42B respectively and input to the vibrator driving circuit 32 via the multiplexer 43.

The aforementioned semi-fixed amplifiers 42R, 42G and 42B are to correct the spectrum strength distribution of the transparent light by the lamp 22, the transfer characteristics of the light guide 16 against the waveform and the light sensitivity of the solid pickup element 4'.

Adjacent to the light shielding plate 25 which is driven by the bimorph vibrators 28 and 29, tri-color filter 44 is provided and the tri-color filter 44 is quickly displaced by the bimorph vibrators 46 and 47 which are driven by the driving signal of the vibrator driving circuit 45.

The tri-color filter 44 consists of red, green and blue color transmitter filters 44R, 44G and 44B which are formed in stripes and can be faced to the openings of the adjacent light shielding plate 25 and are vibrated up and down by the output signal of the bimorph vibrator driving circuit 45. The vibrator driving circuit 45 can be sequentially connected to the color power sources 49R, 49G and 49B by means of the multiplexer 48, and these multiplexers 48 and 43 can be sequentially switched every frame in each color by means of the switching signal of the color frame switching circuit 50. Through the sequential connection to the power sources 49R, 49G and 49B, the amount of displacement changes in stages and the transmitter filter portion of the tri-color filter 44 to correspond to the transmitting part 27B of the flyeye lens 26 is sequentially switched to 44R, 44G, 44B, 44R, . . . , and accordingly, the color of the illuminating light irradiated to the subject through the light guide 16 is sequentially switched to red, green, blue, red, . . .

In this embodiment a black and white solid pickup element 4' is used, and the video processor 9' separates the output signals of the solid pickup element 4' into the color signals R, G and B and records them by switching the output signals per frame with the switching signal of the color frame switching circuit 50 and via a multiplexer, etc., and in the read-out mode they are simultaneously output and displayed on the monitoring color television set 14.

When the endoscope 41 related to the second embodiment thus made up is used, the multiplexers 43 and 48 are switched synchronously and the subject is sequentially lighted in 3 primary colors through the color transmitter filters 44R, 44G and 44B. Then, the subject illuminated in these colors is image-formed on the image pickup face, changed into electrical signal, sequentially output, together with the application of the clock signals from the light receiving elements, by charge transfer or together with the application of the XY address signal, and put into the video processor 9' after amplification. The image is separated into the color signals R, G and B and taken in by the video processor 9' and on the color television set 14 they are displayed simultaneously. At the same time, the dimmer signal is made which does not lose the color balance through the adder 33 and integrating circuit 34, and after the color correction, the amount of displacement of the light shielding plate 25 is automatically controlled for each frame via the vibrator driving circuit 32. Therefore, even in the illumination of each color, a proper intensity of illumination can be automatically controlled.

Since in this embodiment the color correction and automatic light control can be done for each color, truer image pickup or reproduction can be achieved, and since the black and white solid pickup element 4' can use all the light receiving element for the illumination in each color, the resolution can be improved.

Figure 5:
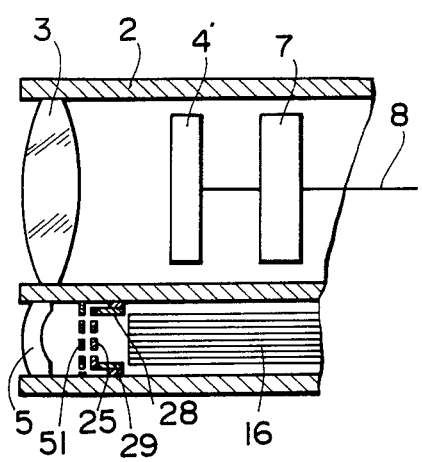
FIG. 5 is a sectional view to show the end of the inserting member of the endoscope related to a third embodiment of this invention, FIG. 6 a sectional view to show the end of the inserting member of the endoscope related to a first embodiment of this invention and FIG. 7 a sectional view to show the end of the inserting member related to a first embodiment.

FIG. 5 shows the end part of the inserting member of an endoscope equipped with the third embodiment of this invention.

In this embodiment, the light shielding plate 25 as shown in FIG. 1 and another light shielding plate 51 facing the light shielding plate 25 are provided between the front end of the light guide 16 and the light distributing lens 15, for example, at the pupil position of the light distributing lens 15. One light shielding plate 51 is fixed and the other light shielding plate 25 is fixed via the bimorph vibrators 28 and 29 and driven by the control signal from the vibrator driving circuit 32 as shown in FIG. 1, to control the quantity of light to be irradiated to a subject via the transmitting portion of these light shielding plates 25 and 51, thus setting the quantity of light to be received by the solid pickup element 4.

Figure 6:
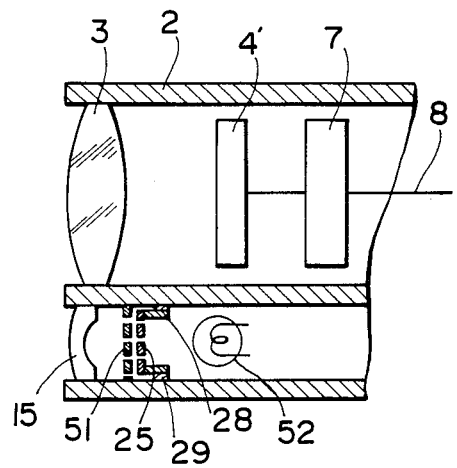

FIG. 6 shows the end part of the inserting member of an endoscope equipped with the fourth embodiment of this invention.

In this embodiment, the light guide 16 in the above embodiment 3 is replaced by the lamp 52 as a lighting means at the tip side of inserting member 2.

As a substitute for the lamp 52, a light emission diode can be used. In such a case, if the 3 primary colors cannot be achieved with a single light emission diode, multiple light emission diodes can be used to make it possible to illuminate in the 3 primary colors.

Figure 7:
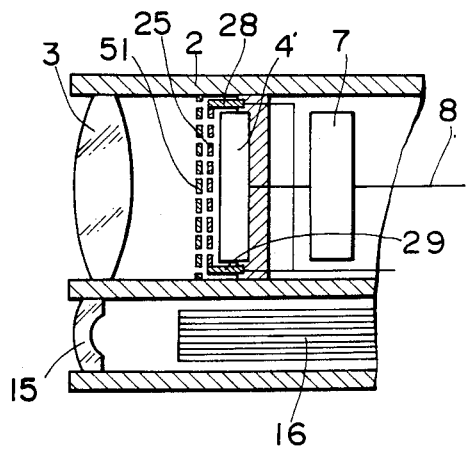

FIG. 7 shows the end part of the inserting member of an endoscope equipped with the fifth embodiment 4 of this invention.

In this embodiment, the light control using the light shielding plates 25 and 51 and the driving means of bimorph vibrators 28 and 29 shown in FIG. 5 are provided before the solid pickup element, and in this case, the automatic control can be achieved by controlling the quantity of light received by the image pickup face.

In FIGS. 5, 6, or 7, the flyeye lens 26 shown in FIG. 1 or 3 can be also used as light-controlling means employing two light-shielding plates 25 and 51.

Both the shielding plates 25 and 51 and be displaced in opposite direction or the shielding plate 25 and flyeye lens 26 can be moved in opposite direction. The light can also be controlled by displacing the flyeye lens 26 side in FIGS. 1 and 3.

In the aforementioned light control member, the light transmitting portion is not limited to the slit opening and it can be circular, square or other opening. The important thing is that the area of the light transmitting portion can be changed. The displacement is not limited to the vertical and horizontal directions and the area of the light transmitting portion can be changed through rotary displacement. Also, the light shielding plate, etc. can be inclined.

Although in the above embodiments, the bimorph vibrators are used as the driving means, ordinary piezoelectric vibrator or the combination of magnet and solenoid (including electromagnet) can also be used.

The solid pickup element is not limited to charge transfer system such as CCD (Charge Coupled Device) and XY address system can also be used.

In the embodiment shown in the above FIG. 3, the adder 33 and integrating circuit 34 can be provided on the output side of the semi-fixed amplifiers 42R, 42G and 42B.

When, as in the case of the fifth embodiment, the automatic light control means is provided on the image pickup means side, it is not limited to those which have the illuminating means such as endoscope and it can be applied to a wide range of optical equipment.

This invention can be applied not only for color but also for black and white.

In the aforementioned first to fifth embodiments, the quantity of illuminating light or the quantity of light incident upon the image pickup face is controlled by means of the passing light changing member using bimorph vibrators, etc. in accordance with the signal level output from the solid pickup element, and therefore, even if the subject observation distance is changed, the light can be controlled to a proper intensity of illuminating light or of the incident light suitable for the observation.

Furthermore, it has simple mechanism and can be made at a low cost and another advantage is that it can be contained in a small space.

The aforementioned embodiments use the vibrating driving means such as bimorph vibrators to form the automatic light control means, but the following will describe the automatic dimmer using liquid crystal filter.

As shown in FIG. 8, in the endoscope 57 equipped with the sixth embodiment, signals to correspond to each picture element passed through the red, green and blue transmitter filter are sequentially output from, for example, 3 output ends, in accordance with the clock signals (read-out signal) applied to the solid pickup element 4 which forms an image pickup means, and the said signals are amplified by the preamplifier 7 with low noise factor, pass through the signal cable 8' and are further amplified by the color amplifiers 9R, 9G and 9B. The above clock signal is output from the signal reading circuit (driving circuit) 58 and it is formed by the reference signal of the reference oscillator 59.

The above reference signal is input to the horizontal deflection circuit 60 and vertical deflection circuit 61, and the horizontal and light control signals are taken in and the signal is output as n digital amount through the comparator which has, for example, n reference levels in stages. By means of the n signal output, the area of the light transmitting portion of the liquid filter 64 is changed and the quantity of illuminating light can be automatically controlled.

On one side of the liquid crystal 64, a clear electrode is formed on the entire surface and on the other side, n clear electrodes are formed in stripes as shown in FIG. 9 and the n clear electrodes are repeated at a certain interval and the mutually corresponding stripe electrodes are conductively connected with a lead wire to become n electrodes as a whole.

For the liquid crystal filter 64, the number of electrodes to which the voltage is applied changes in accordance with the number of high levels of the n signals output from the liquid crystal driving circuit 65, and as shown in FIG. 9, as the number of the high levels increases from 0 (FIG. 9 (a)), the area of the light transmitting portion becomes smaller as shown in (b) and further smaller as shown in (c) (the area of the light shielding portion becomes wider).

In FIG. 9, the aventurine portion shows the clear electrode portion in stripes and the oblique line portion the light shielded portion after the high level voltage is applied.

In the endoscope 57 equipped with the sixth embodiment thus made up, if the intensity of illumination is too high such as when the distance to a subject such as affected part is too short or when the reflecting strength of part of the affected part is too high, the level of the dimmer signal coming through the integrating circuit 34 is high, and in accordance with the size of the said level, the vertical deflection signals are formed from the n output ends of the liquid crystal driving circuit 65 and applied to the X and Y deflection terminals of the color CRT 62 and displayed on the color CRT 62 while the red, green and blue color signals R, G and B output from the color amplifiers 9R, 9G and 9B are being sweeped horizontally and vertically.

By the way, in the light source unit 63 in which the rear end of the light guide 16 is installed, at the pupil position of the condenser lens 24 on the light path of the luminous flux which is made parallel by the reflector 23, a liquid crystal filter (liquid crystal plate) 64 is provided, and when a voltage is applied, the liquid crystal portion between the electrodes to which the voltage is applied becomes light shielding portion and thus the area of the light transmitting portion is changed.

The liquid crystal filter 64 is provided with, for example, n electrodes and these electrodes are connected to the n output ends of the liquid crystal driving circuit 65. In this liquid crystal driving circuit 65, the number of high levels in the analog signals formed on basis of the color signals R, G and B increases and the light shielding area of the liquid crystal filter 64 increases and the intensity of the light illuminated through light guide 16 to a subject decreases. Therefore, after one frame, a proper intensity of illumination is obtained and the color picture with proper contrast can be obtained. On the contrary, in the case of dark color picture with low contrast, the level of the dimmer signal becomes low to increase the intensity of illumination, thus automatically setting to a proper intensity as explained above.

Therefore, it does not require the manual adjusting work as in the case of the conventional types, and accurate diagnosis can be made always in an easy-to-see state.

Even in the case of such excessive illumination as to cause the blooming phenomenon, the automatic dimmer function quickly operates to prevent the blooming phenomenon. Also, it has such advantages as simple structure and low cost.

Figure 10:
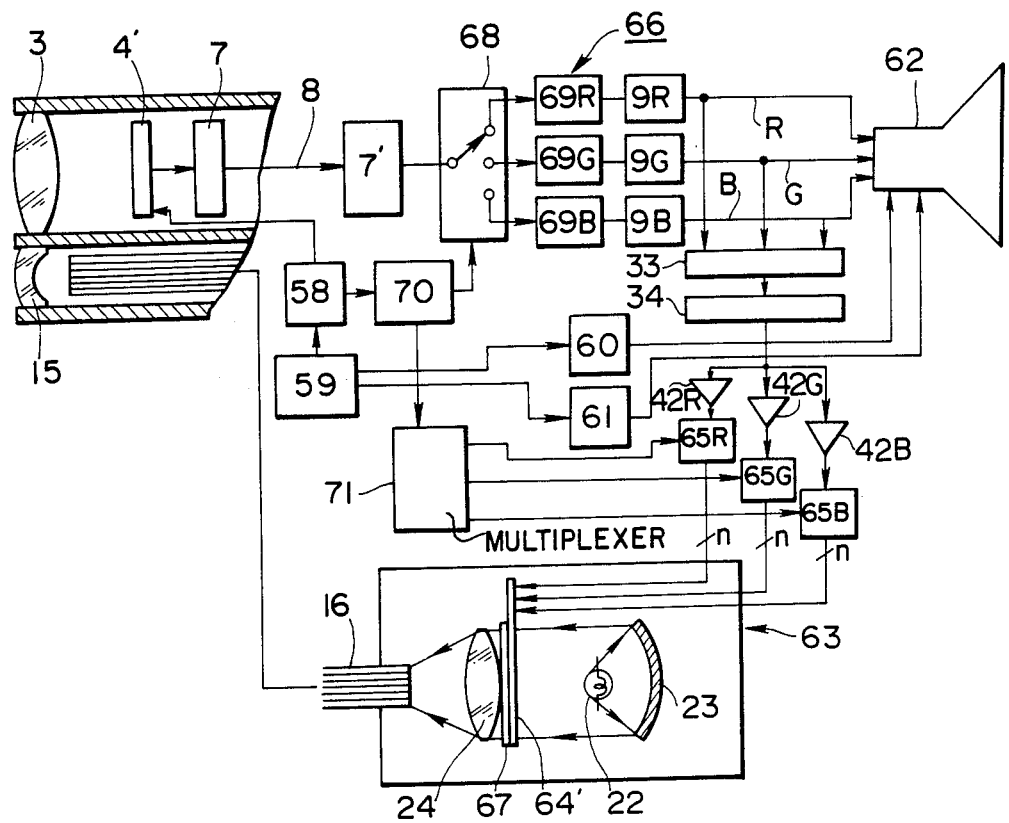
FIGS. 10, 11 and 12 concern a seventh embodiment of this invention, FIG. 10 being an explanatory drawing to show the makeup of the entire endoscope using the seventh embodiment, FIG. 11 a front view to show the tri-color filter and FIG. 12 an explanatory drawing to show the liquid crystal plates.

FIG. 10 shows an endoscope equipped with the seventh embodiment of this invention.

In the endoscope 66 equipped with this embodiment, a monochrome (black and white), solid pickup element 4' is used and in the light source unit 63, a tri-color filter 67 is provided in close contact with the liquid crystal (liquid crystal plate) 64' at the pupil position of the condenser lens 24 so that it is possible to illuminate in the light of 3 primary colors (wavelength).

Figure 11:
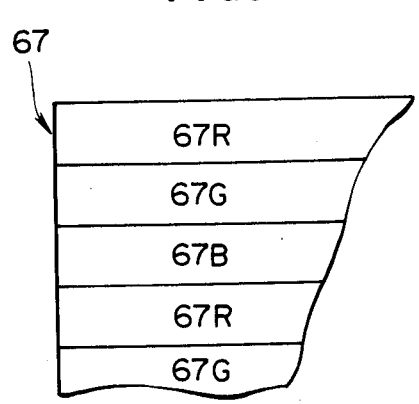

In the tri-color filter 67, for example, as shown in FIG. 11, red transmitter filter 67R to pass the red color light only, green transmitter filter 67G to pass the green color light only and blue transmitter filter 67B to pass the blue color light only are provided in stripes, sequentially repeated.

Figure 12:
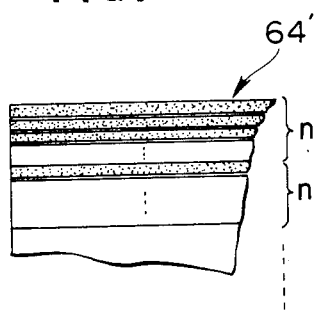

The liquid crystal plate 64' provided in contact with the tri-color filter 67 is divided into n electrodes as in the embodiment 1, at the portions to come into contact with the stripe portions in the color transmitter filters 67R, 67G and 67B (see FIG. 12), and the electrode portions to correspond to the same color filter portion are conductively connected to form n electrodes against the color transmitter filters 67R, 67G and 67B, and by means of the high level voltage applied to these electrodes the light shielding portion is formed to change the quantity of the light transmitted, thus changing the intensity of the light illuminating the subject or to change the quantity of light to be received by the solid pickup element 4'.

The reflected light which is received by the solid pickup element 4' from the subject illuminated in the light of each color through the combination of the tri-color filter 67 and liquid crystal plate 64' is amplified by the preamplifier 7 and further amplified by the color amplifier 7' via the signal cable 8 and is stored in the color frame memories 69R, 69G and 69B via the multiplexer 68.

The color signals R, G and B read from the frame memories 69R, 69G and 69B are amplified by the color amplifiers 9R, 9G and 9B and input to the color CRT 62 and at the same time they are input to the semi-fixed amplifiers 42R, 42G and 42B via the adder 33 and integrating circuit 34 as shown in FIG. 3. The outputs from the semi-fixed amplifiers 42R, 42G and 42B are applied to the input ends of the liquid crystal driving circuits 65R, 65G and 65B. The multiplexer 68 is controlled by the color switching circuit 70 which outputs a switching signal every time the signal of the picture element of 1 frame in each color is read, on basis of the clock signal from the driving circuit 58, and these switching signals are applied to the control ends of the liquid crystal driving circuits 65R, 65G and 65B via the multiplexer 71. In the liquid crystal driving circuit to which the switching signal is not applied or via an analog switch added, etc., all the n output ends output high level voltage and all the electrodes of the liquid crystal plate 64' connected to the said output ends are light-shielded. 2 filters in the tri-color filter 67 are set to the above state while changing the combination, and the remaining filter takes part in the automatic dimmer function.

If the frame memories 69R, 69G and 69B are digital memory, the wiring is done through an A/D converter and the reading through a D/A converter to produce the analog amount and then the display is made on the color CRT 62.

In the seventh embodiment make up, if the multiplexer 68 is connected to the red frame memory 69R as shown in FIG. 10, the liquid crystal driving circuit 65R for the red color is made ready to operate and all the n output ends of the other liquid crystal driving circuits 65G and 65B output high level signals and the liquid crystal plate 64' portion in contact with the green and blue transmitter filters 67G and 67B are shielded. Therefore, the illuminating light of the lamp 22 passes through the transmitting portion of the liquid crystal plate 64' and becomes the light of red color only through the red transmitter filter 67R and the subject is illuminated in that light. The light reflected from the subject is image-formed on the image pickup face of the solid pickup element 4' by the object lens 3, and the output signals of the light receiving elements together with the applied clock signals are amplified and via the multiplexer 68, written in the red frame memory 69R. The red color signal R through the multiplexer is written in the frame memory 69R.

Then, the image picked up in the green light through the green transmitter filter 67G is written in the green frame memory 69G. And the image signal picked up in the blue light is written in the blue frame memory 69B.

The signals written in the frame memories 69R, 69G and 69B are read out simultaneously and displayed on the color CRT 62, and at the same time, they are input to the liquid crystal driving circuits 65R, 65G and 65B via the adder 33 and integrating circuit 34 and through the semi-fixed amplifier circuits 42R, 42G and 42B. Thus, in accordance with the level of the dimmer signal of one previous frame, the liquid crystal plate 64' is automatically set in a proper light transmitting state.

Figure 13:
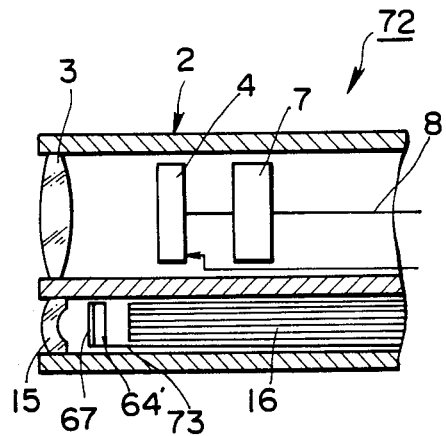
FIG. 13 is a schematic sectional view to show the important part of an eighth embodiment.

FIG. 13 shows the end side of the inserting member of the endoscope related to the eigth embodiment of this invention.

In the endoscope 72 equipped with the eigth embodiment, the tri-color filter 67 and liquid crystal plate 64' in the aforementioned seventh embodiment are not contained in the light source unit 63 but provided between the front end of the light guide 16 and the light distributing lens 15, for example, at the pupil position of the said light distributing lens 15 and are connected to the liquid crystal driving circuits 65R, 65G and 65B (shown in FIG. 10) via the lead wire bundle 73.

The action effect of this embodiment is same as that of the seventh embodiment.

Figure 14:
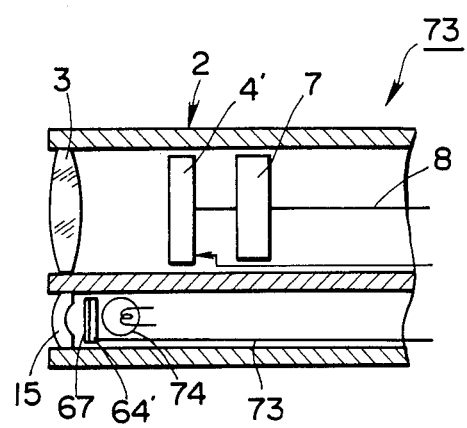
FIG. 14 is a schematic sectional view to show the important part of a ninth embodiment.

FIG. 14 shows the end side of the inserting member of the endoscope related to the ninth embodiment of this invention.

In the endoscope 73 of this embodiment, the light guide 16 in the embodiment 8 is not used, and instead, a light emission diode (including 3 primary colors and not limited to a single diode and multiple diodes can also be used) or lamp 74 is provided behind the tri-color filter 67 and liquid crystal plate 64'. The remaining structure remains same as that of the eighth embodiment. This embodiment has the same advantage as that of the eighth embodiment that it can be contained in the small inserting member 2.

Figure 15:
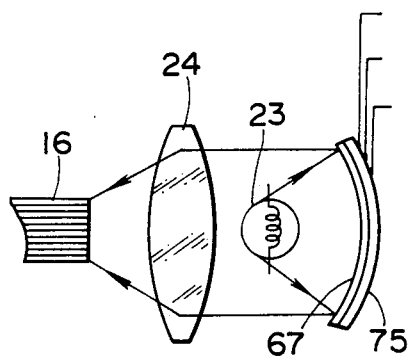
FIG. 15 is a schematic sectional view to show the important part of a tenth embodiment.

FIG. 15 shows the important part of the tenth embodiment 10 of this invention.

In this embodiment, the tri-color filter 67 and liquid crystal plate 75 are used as the reflector in embodiment 6.

That is, a concave liquid crystal plate 75 and tri-color filter 64 in contact with it on the concave side of the liquid crystal plate 75 are provided in the path of the light illuminated from the illuminating lamp 22. In such a case, the liquid crystal plate 75 becomes the light transmitting portion at the part to which the voltage is applied, and if no voltage is applied, the light is reflected and the illuminating light of each color filtered is irradiated to the incident end of the light guide 16 through the condenser lens 24.

This embodiment has approximately the same action effect as that of the seventh embodiment.

Figure 16:
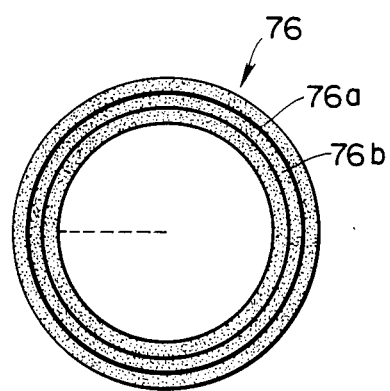
FIG. 16 is an explanatory drawing to show the other embodiment of the liquid crystal filter.

This invention is not limited to the aforementioned, and for example, the light transmitting portion or reflecting portion of the liquid crystal filters (liquid crystal plates) 64 and 64' is not limited to the stripe, but can be a circular liquid crystal filter 76 as shown in FIG. 16. That is, the concentric circles 76a, 76b . . . can be changed from light transmitting portion to shielding portion or from reflecting portion to transmitting portion by applying the voltage.

Also, mesh or other shape can be acceptable.

As aforementioned, the sixth to tenth embodiments have automatic light controlling means which can adjust the intensity of light to illuminate the subject by controlling the transmission area of the liquid crystal filter in accordance with the dimmer signal, and therefore, the image pickup and color reproduction can be achieved at a proper brightness without causing the blooming phenomenon.

The aforementioned embodiments use the automatic light controlling means which automatically set to a proper value the intensity of the light to illuminate the subject or intensity of the incident light to be received by the image pickup means, but the following will describe the automatic dimmer equipment which controls the light receiving period in case the color face sequential lighting system.

The end side of the inserting member 2 of the endoscope 81 equipped with eleventh embodiment shown in FIG. 17 includes a line transfer type solid pickup element 84 whose light sensing part 82 is common with the transfer part as shown in FIG. 18. The solid pickup element 84 consists of the light sensing part 82 and output part 85, and the light sensing part 82 for 1 frame is formed by forming in multi-stages in vertical direction the light receiving elements arranged in horizontal direction, and on one end of the element lines, a shift register to be the output part 83 is provided. And for each line, the transfer signal is switched to take out the signal. Since this line transfer type solid pickup element 84 does not require the transfer part different from the light sensing part 82, it can be made compact and is suitable for the endoscope.

On the end side of the long and narrow inserting member 2, a light shielding member 86 as light quantity changing member is provided between the object lens 3 and the solid pickup element 84 at the pupil position of the object lens 3. This light shielding member 86 is, for example, a shutter using the liquid crystal panel, and for example, when low level voltage or no voltage is applied, it is controlled to create the light shielding state, and the signal output from the solid pickup element 84 by means of the pulse signal applied through the drive circuit 58 is input to the video processor 9 via the preamplifier 7. This video processor 9 consists of the amplifier 7' to amplify the output signal of the preamplifier 7, multiplexers (or switches) 68R, 68G and 68B to selectively connect the output ends of the amplifier 7', and the frame memories 69R, 69G and 69B which are sequentially connected conductively by means of the multiplexers.

The above frame memories 69R, 69G and 69B are sequentially placed in the write mode and simultaneously placed in the read mode and the signals are input to the color television set 14 and displayed in color.

The dimmer signal forming means 87 consists of the 1st adder 33, integrating circuit 34, 2nd adder 88 to one input end of which the output Y of the integrating circuit 34 is applied, and color correction circuit 89 whose color correction voltage $V_{RGB}$ is applied to the other input end of the adder 88.

This color correction circuit 89 generates the color correction volta $V_{RGB}$ to correspond to each color signal for each frame period so that each color signal obtained by means of the illuminating light of each waveform irradiated by the illuminating means to be described later will be displayed in a proper hue.

The output of the dimmer signal forming means 87, i.e. the output of the 2nd adder 88 is input to the pulse width modulator 91, part of the receiving light control means 90. The pulse width modulator 91 to which the accumulated pulse 91a generated during the light accumulation period of the solid pickup element 84 is applied through terminal 90a modulates the said accumulated pulse 91a into a specified pulse width without changing the rise time in accordance with the output 88a of the 2nd adder 88 and sends it out as the control pulse CP to the next stage. The control pulse CP which has been made by modulation of this accumulated pulse 91a is input to the transmitting and shielding driving part 92. This transmitting and shielding driving part 92 amplifies the control pulse CP and applies it as transmitting and shielding driving signal 92a to the light shielding member 86.

On the other hand, to the incident end of the light guide 16, the illuminating light from the strobo equipment using a xenon lamp 22' driven by the light source unit 93 is supplied through the condenser lens 24 and rotary filter 94 after reflected by the reflector 23.

This rotary filter 94 is, for example, a disk provided with filter arranged at equal intervals which pass the light of red, green and blue waveforms and sequentially switches the illuminating light from the condenser lens 24 into red light, green light and blue light. The rotary filter 94 is driven by the motor 95 and via the transfer mechanism 96, and the rotation is made by intermittently driving the motor 95, for example, with the gate pulse used for change-over driving of the multiplexers 68R, 68G and 68B so that it corresponds to the 1 frame period of the solid pickup element 84. The rotary filter 94 is so set that the color switching time will be during the transfer period (read-out period) of the solid pickup element 84 (in this embodiment it is made in agreement with the starting time of the transfer period Tr) as shown in FIG. 19.

The operation of the automatic dimmer made up as above will be described referring to FIG. 19. FIG. 19 shows the waveforms of the parts of the endoscope 81 in FIG. 17 and the rotation is made intermittently so that each filter of the rotary filter 94 is on the light path for each frame period T. The red, green and blue rays illuminate the subject and the rays reflected by the subject hit the light sensing part 82 of the solid pickup element 84. The light sensing part 82 of the solid pickup element 84 accumulates the inside image by each ray as signal charge, and transfers the accumulated signal charge by means of the transfer pulse (signal of transfer period $T_R$) and outputs it as series data from the output part 85. This output becomes the picture signal which changes as red signal, green signal and blue signal for each frame period T. The picture signals are input to the multiplexers 68R, 68G and 68B via the preamplifier 7 and amplifier 7' and input to the frame memories 69R, 69G and 69B through the time sharing switching operation of the multiplexers 68R, 68G and 68B which are synchronized with the frame period. The color signals read from these frame memories 69R, 69G and 69B are displayed on the television receiver 14 and at the same time input to the 1st adder 33. The 1st adder 33 adds the input when one or two of the red, green and blue signals are received and sends them out to the integrating circuit 34.

Figure 19:
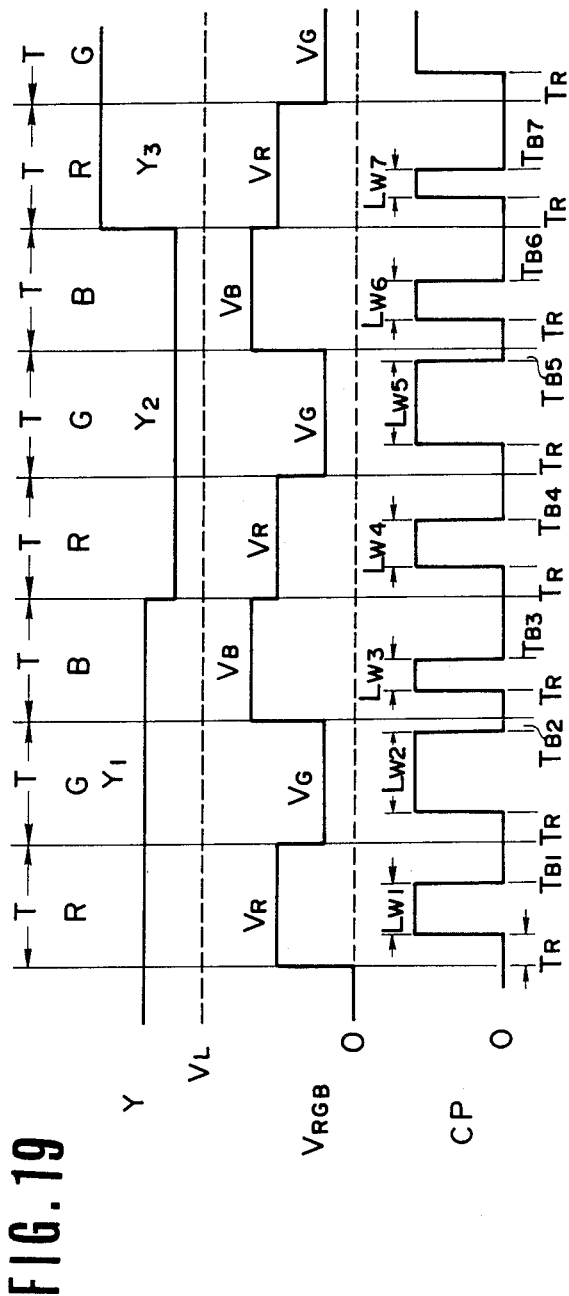
FIG. 19 is a waveform drawing to explain the operation of each part in FIG. 17.

Luminance output Y of the integrating circuit is shown in FIG. 19. The luminance output Y is a DC voltage which does not become lower than a certain reference level $V_L$, and the voltage level is renewed as $Y_1$, $Y_2$, $Y_3$ for every three frames as shown in FIG. 19. This luminance output Y can be directly input to the pulse width modulator 91, but in this embodiment it is added to the color correction voltage $V_{RGB}$ from the color correction circuit 89 by the 2nd adder 88. This color correction voltage $V_{RGB}$ shows the voltage levels $V_R$, $V_G$ and $V_B$ corresponding to the irradiation period of the red, green and blue rays, and this makes it possible to reproduce the picture signal as optimum picture of the red, green and blue colors synthesized. Therefore, the output 88a of the 2nd adder 88 becomes $Y_1+V_R$ color correction voltage, i.e. luminance output Y of $Y_1$ level plus color correction volta $V_{RGB}$ of $V_R$ and the voltage is input to the pulse width modulator 91.

Since to this pulse width modulator 91, the accumulated pulse 91a synchronized with the accumulation period is applied, the output 88a of the send adder 88 can change the pulse width of the accumulated pulse 91a in accordance with the adder output level. This changed accumulated pulse 91a is formed as the control pulse CP as shown in FIG. 19. That is, the control pulse CP is, for example, as shown in FIG. 19, such a signal to show the pulse width $L_{W1}$ for the adder output $V_1+V_R$ and pulse width $L_{W2}$ for the adder output $Y_1+V_G$. The rise time of these pulses starts always after a certain period $T_R$ with the beginning of 1 frame period T as the reference. The period $T_R$ is equivalent to the transfer period of the frame transfer type solid pickup element and is usually longer than $T_2$. The rotary filter 94 switches the illuminating light from the strobo lamp 22' when this transfer period $T_R$ starts. And the control pulse CP of the pulse width Lw1, Lw2, Lw3 ... which rose after the period $T_R$ is amplified by the transmitting/shielding driver 92 and applied as transmitting/shielding driving signal 92a to the liquid crystal shutter of the light shielding member 86. This liquid crystal shutter becomes transparent to irradiate the light reflected from the subject to the solid pickup element 84 during the control pulse CP is at high level, i.e. during the pulse width Lw1, Lw2, Lw3 ... of the accumulated pulse 21a in accordance with the added level of the luminance output Y and color correction voltage $V_{RGB}$. And after the period of the pulse width Lw1, Lw2, Lw3 ..., the control pulse CP, i.e. the transmitting/shielding signal 92a becomes low level to blind the liquid crystal shutter. The blind state continues until the completion of 1 frame and can shield the incident light to the solid pickup element 84. When the light incident upon the solid pickup element 84 is too strong, the output level of the picture signal obtained by the solid pickup element 84 increases and the integrating circuit 34 increases the luminance output Y and the adder output 88a of the 2nd adder 88 becomes high level. If this level is high, the pulse width Lw1, Lw2, Lw3 ... of the control pulse CP decrease and on the contrary the non-receiving periods $T_{B1}$, $T_{B2}$, $T_{B3}$ ... of the solid pickup element 84 increases. Therefore, the light receiving can be stopped before the blooming phenomenon occurs and good picture without smearing of color can be obtained.

Since the time when the solid pickup element 84 starts transferring is made in agreement with the time to switch the color of the illuminating light and the transfer period $T_R$ is made in agreement with the original shielding period (blind state), at the same time when the illuminating light is switched, the signal charge accumulated during the previous period can be transferred and read (output) during the following transfer period $T_R$, as in this embodiment, and after the transfer is completed, the light shielding member 86 can be made transparent in accordance with the specified pulse width Lw1, Lw2, Lw3 ..., thereflected light from the subject can be put in the solid pickup element 84, and the light receiving and accumulating operation can be done. Therefore, when the illuminating light is switched, the color signal of the adjacent frame will not be mixed with the signal charge being transferred and no smearing will occur.

The transfer period $T_R$ can also be set at the end of each frame. Also, as shown in alternate long and two short dashes line in FIG. 17 in the eleventh embodiment of this invention, it is also possible to prepare the signal equivalent to the accumulated pulse 91a by inputting the vertical synchronizing pulse to the terminal 97 and inputting the vertical synchronizing pulse to the transmitting/shielding driving signal forming circuit 98 and to modulate the pulse width of the signal with the adder output 88a from the second adder 88. In such a case, the pulse width modulator 91 is omitted and the adder output 88a from the 2nd adder 88 is directly input to the transmitting/shielding driving signal forming circuit 98.

Figure 20:
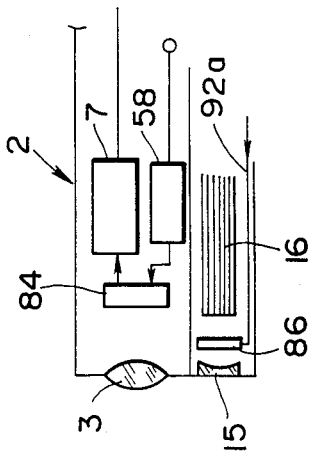
FIG. 20 is an explanatory drawing to show the important part of a twelvth embodiment of this invention, FIGS. 21 to 24 concern a thirteenth embodiment of this invention, FIG. 21 being a block diagram to show an endoscope equipped with the thirteenth embodiment, FIG. 22 an explanatory drawing to show a mosaic type filter provided on the image, pickup face of the solid pickup element.

The important part of twelfth embodiment of this invention is shown in FIG. 20. The same symbols are used for the same elements as those shown in FIG. 17. FIG. 20 shows the end part of the endoscope 81', and in front of the irradiating end of the light guide 16 a light shielding member 86 such as liquid crystal shutter is provided. This light shielding member 86 is shut or opened by the transmitting/shielding driving signal 92a from the transmitting/shielding driver 92 which forms the light quantity control means 90 shown in FIG. 17.

Since this embodiment can shut off the illuminating light of the light guide 16 during the transfer period $T_R$ of the solid pickup element 84 and control the light transmitting period with the pulse width of the light shielding driving signal 92a, the blooming can be prevented and the false signal due to the reflected light from the subject is not accumulated in the signal charge being transferred. The light shielding member 86 can also be located on the incident end of the light guide 16.

As explained above, in the eleventh and twelfth embodiments, the switching time of the illuminating light is set to correspond to the transfer period and the light receiving is stopped during the transfer period and the light receiving time during the accumulating period is controlled in accordance with the output level of the picture signal obtained by the solid pickup element 84, and therefore, the color mixing and smearing when the illuminating light is switched can be prevented and the blooming phenomenon does not occur.

Figure 21:
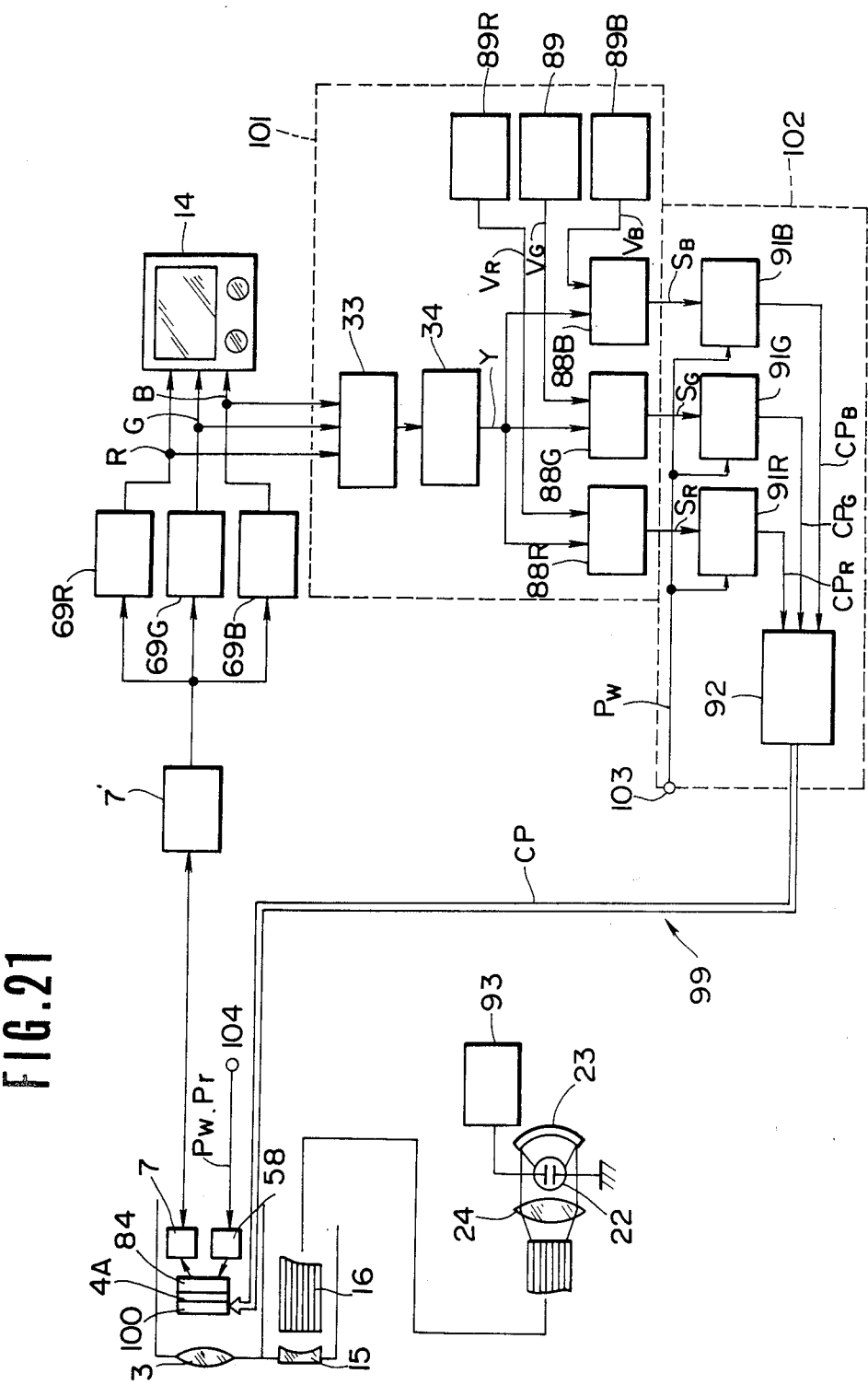

FIG. 21 shows a endoscope 95 equipped with thirteenth embodiment of this invention.

In this endoscope 99, the line transfer type solid pickup element 84 as in the eleventh embodiment 11 (shown in FIG. 18) is used and, as the light controlling member, the liquid crystal shutter 100 which can control the light transmission and shielding is provided at the light sensing part 82 of the solid pickup element 84.

Figure 22:
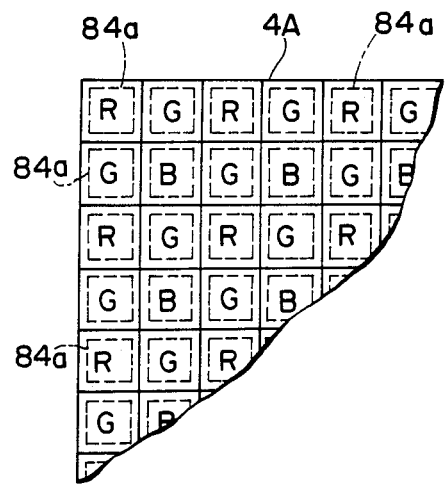

That is, a mosaic filter 4A is fitted to the light sensing part (pickup face) of the solid pickup element 84 contained in the end part of the inserting member 2. In this filter 4A, as enlarged in FIG. 22, for each light receiving element 84a, 84a, ... to correspond to each picture element, the color transmitter filter picture elements (R, G and B in FIG. 22) each of which transmits the light of each color (waveform) only such as red, green or blue are arranged in accurately corresponding way, for example, Bayer arrangement. On this filter 4A the liquid crystal shutter 100 is attached with adhesive, etc.

The liquid crystal shutter 100 consists of the light shielding elements 100R, 100G, 100B ... formed to correspond to the filter picture elements, and the light shielding elements 100R, 100R ..., 100G, 100G ... or 100B, 100B ... formed to correspond to each filter picture element of the same color are connected conductively to form the same controlling electrode and in accordance with the low level or high level of the applied voltage, the light shielding state or transmitting state can be achieved.

The output signal of the solid pickup element 84 is written in the analog type color frame memories 69R, 69G and 69B so as to become separated color signals. This writing is done during the transfer periods shown in FIG. 24. The signals written in the color crame memories 69R, 69G and 69B are read simultaneously during the accumulating period Tw of the solid pickup element 84 and the read color signals R, G and B are applied to the RGB input ends of the color television receiver 14. The color signals R, G and B are also supplied to the dimmer signal forming means 101. The dimmer signal forming means 101 consists of the 1st adder 33, integrating circuit 34, 3 adders 88R, 88G and 88B to one input end of which the output Y of the integrating circuit 34 is applied, and color correction circuits 89R, 89G and 89B which apply the color correction voltages $V_R$, $V_G$, and $V_B$ to the other input end of the adders 88R, 88G and 88B.

The outputs $S_R$, $S_G$ and $S_B$ of the adders 88R, 88G and 88B are input respectively to 3 pulse width modulators 91R, 91G and 91B which form the light control means 102. The outputs $CP_R$, $CP_G$ and $CP_B$ of the pulse width modulators 91R, 91G and 91B are input to the liquid crystal driver 92 and the output of the liquid crystal driver 92 controls the shielding or opening of the light shielding elements 100R, 100G, 100B ... of the liquid crystal shutter 100.

To the 3 pulse width modulators 91R, 91G and 91B, the accumulated pulse Pw to drive, for example, the solid pickup element 84 is input from the terminal 103 as the signal for pulse width modulation, and the accumulated pulse Pw is generated by the element control logic circuit (not illustrated). As the signal for modulation, it is also possible to use the vertical synchronizing pulse besides the accumulated pulse Pw. The accumulated pulse Pw is supplied to the terminal 104 together with the transfer pulse Pr, another driving pulse of the solid pickup element 84 and applied to the specified electrode of the solid pickup element 84 through the driving circuit 58.

Figure 24:
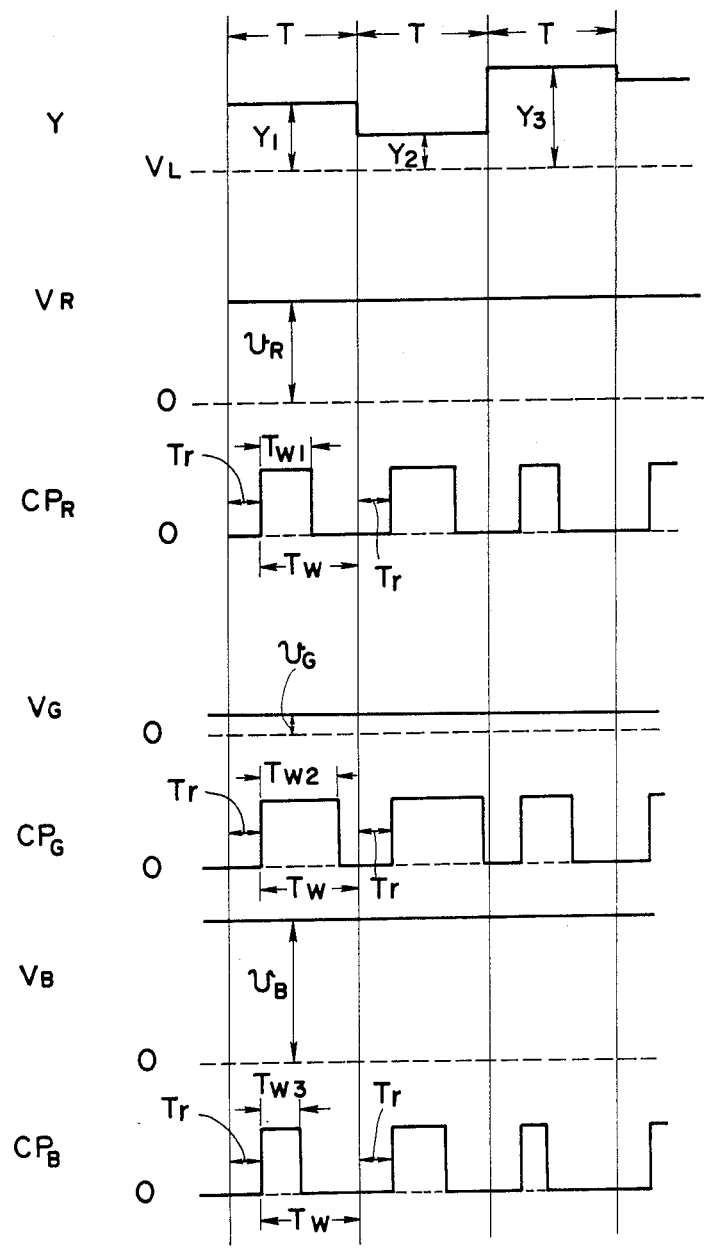

The following will describe the operation of the endoscope 99 equipped with the thirteenth embodiment referring to FIG. 24. In FIG. 24, the symbol T indicates one frame period, and the voltage level of the integrated output Y of the integrating circuit 34 is renewed such as $Y_1$, $Y_2$ and $Y_3$ for each frame. These voltage levels $Y_1$, $Y_2$ and $Y_3$ are the output level for each frame period of the luminance output to which each color signal of the picture signal obtained by the solid pickup element 84 is added and are always higher than a certain voltage level $V_L$. The color correction voltages $V_R$, $V_G$ and $V_B$ of the color correction circuits 89R, 89G and 89B are set to the voltage levels $v_R$, $v_G$ and $v_B$. The symbol Tr indicates the transfer period of the solid pickup element and Tw the accumulation period. The transfer period Tr is set to a certain period of the beginning of 1 frame. That is, the solid pickup element 84 can read out the signal charge accumulated during the previous frame period, as picture signal, when it is placed in the transfer mode during a certain period from the start of the following frame period.

This picture signal is input to the color frame memories 69R, 69G and 69B. The picture signals stored as tri-color R, G and B signals in these frame memories 69R, 69G and 69B are read out during the accumulation period Tw of the solid pickup element 84, input, for example, as the signals of 1 field of the television screen to the television receiver 14 and displayed in color.

On the other hand, the R, G and B signals input to the adder 33 become luminance output after color signals are added, and are output from the integrating circuit 34 as the integrated output Y in accordance with the output level. This integrated output Y is input to 3 adders 88R, 88G and 88B.

These 3 adders 88R, 88G and 88B add the integrated output Y to the color correction voltage $V_R$, $V_G$ and $V_B$ of 3 color correction circuits 89R, 89G and 89B respectively. For example, the integrated output Y of $Y_1$ level and the color correction VR of $v_R$ level become $Y_1+v_R$ adder output 88a to control the 1st pulse width modulator 91R. That is, the accumulated pulse Pw (not illustrated) in the 1st, 2nd and 3rd pulse width modulators 91R, 91G and 91B is a pulse which rises approximately at the same time when the transfer period Tr of the solid pickup element 84 is completed and the rise time is constant related to the 1 frame period T. And the aforementioned $Y_1+v_R$ adder output 88a controls the 1st pulse width modulator 91R so as to change the fall time of the accumulated pulse Pw in accordance with the level $Y_1+v_R$. Then the pulse width of the modulated pulse $CP_R$ of the 1st pulse width modulator 91R becomes, for example, Tw1 as shown in FIG. 24. The modulated pulse $CP_R$ of the pulse width Tw1 is applied to the specified electrode formed in the light shielding elements 100R, ... of the liquid crystal shutter 100 as the control signal via the liquid crystal driver 92. This places the light shielding element 100R, ... of the liquid crystal shutter 100 in light transmitting state. And when the modulated pulse $CP_R$ of the pulse width Tw1 falls, the aforementioned elements 100R, ... are placed in light shielding state as shown in slant lines in FIG. 23 (a) and the image of the subject is not formed on the light receiving elements 84a corresponding to the filter picture element (shown by R) of the mosaic color filter 4A.

Figure 23A:
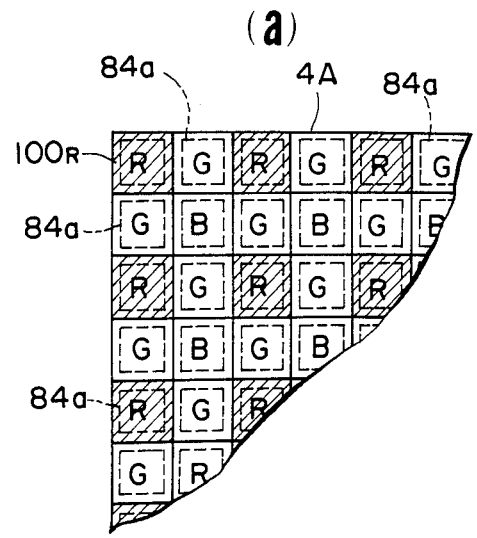
FIGS. 23a, 23b and 23c are explanatory drawings to show that the liquid crystal shutter provided on the mosaic type filter is put into light shielding state and light transmitting state, and FIG. 24 a waveform drawing to explain the operation of the parts in FIG. 22.
Figure 23B:
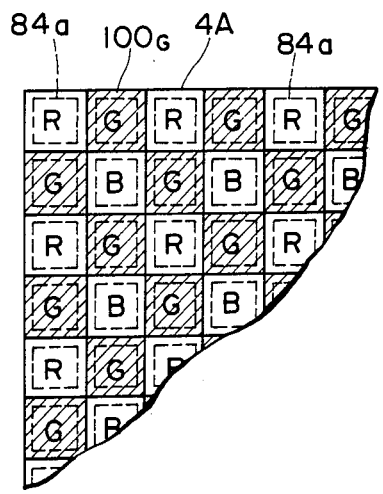
Figure 23C:
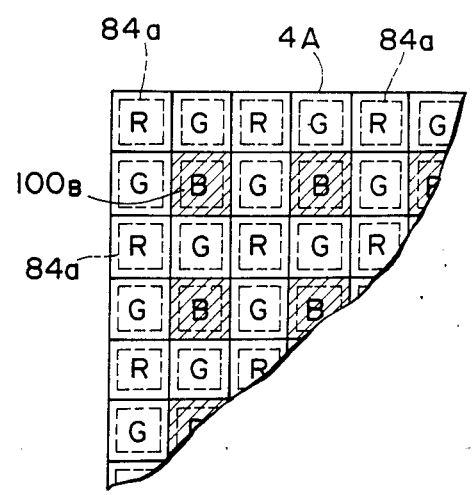

And at the same time, the $Y_1+v_G$ adder output $S_G$ makes the modulated pulse $CP_G$ of pulse width Tw2 and the $Y_1+v_B$ adder output $S_B$ makes the modulated pulse CPhd B of pulse width Tw3, and therefore, the light shielding elements 100G ... and 100B ... of the liquid crystal shutter 96 are placed in light shielding state after the pulse widths Tw2 and Tw3 of the modulated pulses $CP_G$ and $CP_B$ as shown in slant lines in FIG. 23 (a) and (b).

If the integrated level $Y_1$ is the level detected because the light incident upon the solid pickup element 84 becomes too strong, the accumulation period Tw, i.e. light receiving period can be shortened separately for R, G and B against the incident light, thus making it possible to prevent the blooming while achieving optimum color reproduction.

During the transfer period Tr, the accumulated pulse Pw is low level, and therefore, all the light shielding elements 100R ..., 100G ... and 100B ... of the liquid crystal shutter 100 are placed in light shielding state, thus preventing the false charge due to smearing from being added to the signal charge being transferred and the occurrence of color mixing.

This invention can prevent the blooming and smearing in the aforementioned way.

The dimmer signal forming means 101 can also be made up in such a way that the output of the integrating circuit 34 is directly input to the pulse width modulator eliminating the color correction circuits 89R, 89G and 89B. In such a case, only one pulse width modulator is enough.

In the thirteenth embodiment, one light shielding element corresponds to one light receiving element, but it is also possible that one light receiving element corresponds to multiple light shielding elements, and the following will describe such embodiment.

Figure 25:
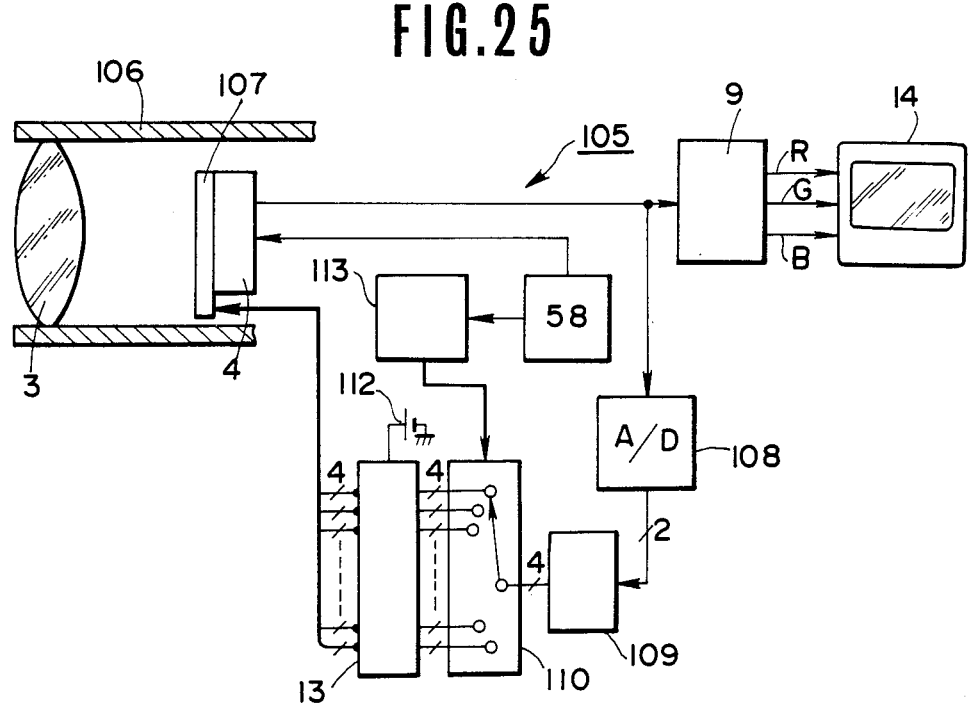
FIGS. 25 to 27 concern a fourthteenth embodiment of this invention, FIG. 25 being a block diagram to show the image pickup equipment provided with the embodiment 14, FIG. 26 an explanatory drawing to show the liquid crystal filter provided on the image pickup face of the solid pickup element and FIG. 27 a circuit diagram to show the makeup of the liquid crystal driving circuit.

FIG. 25 shows an image pickup equipment provided with fourteenth embodiment.

The image pickup device 105 has an object lens 3 for image forming in the lens cylinder 106 and a solid pickup element 4 at the image forming position of the object lens 3.

On the image pickup face of the solid pickup element 4 many light receiving elements are regularly arranged, and each picture element in the optical image formed on the said pickup face is converted into the electrical signal corresponding to the picture element, and by means of the clock signal applied from the driving circuit 58 the output signals of the light receiving elements arranged, for example, in horizontal lines, can be sequentially taken out. To the image pickup face, mosaic type tri-color filter (not illustrated) is fitted, and by passing through the tri-color filter, the signals are taken in as color picture signals of 3 primary colors, amplified by a preamplifier (not illustrated) contained inside or outside the lens cylinder 106, further amplified in the video processor 9, then divided into each color picture signal by the sample hold circuit in the video processor 9, pass through the color amplifier, then superimposed on with horizontal and vertical synchronizing signals, and displayed as 3 primary color signals R, G and B on the color television receiver 14 for monitoring.

On the front face of the tri-color filter, the liquid crystal filter (liquid crystal shutter) 107 to form the embodiment 14 is provided.

Figure 26:
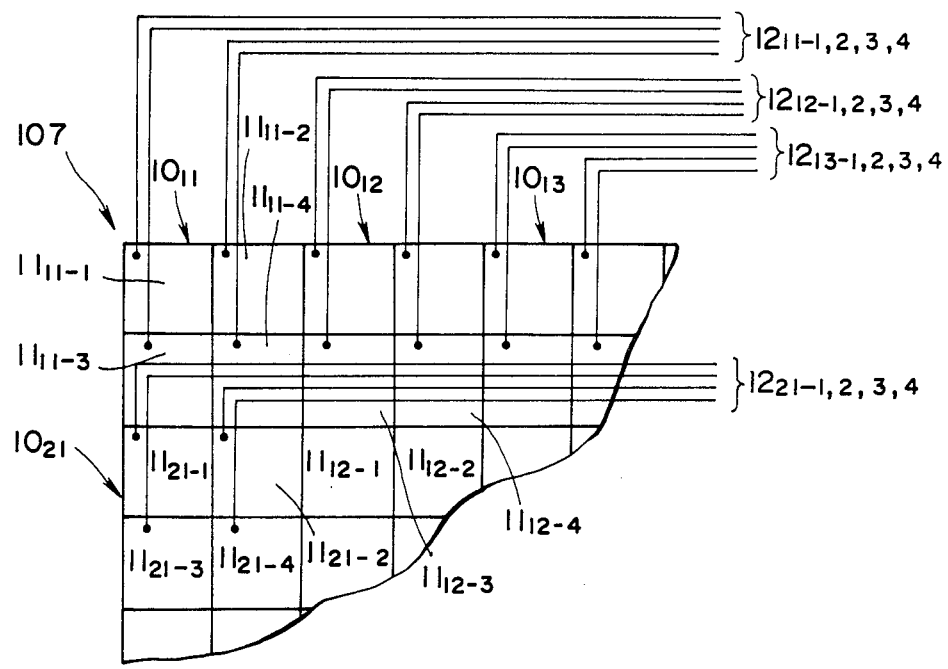

In the liquid crystal filter 107, the light receiving elements arrangement on the image pickup face are regularly covered, for example, with square liquid crystal blocks 10nm (shown in thick solid line) as shown in FIG. 26, and over the entire surface of one side (side not shown in the figure) of the block 10nm of nth row and mth column, clear electrode is attached, and the other side is divided, for example, into two horizontally and vertically to form 4 divided electrode parts 11 nm-1, 11 nm-2, 11 nm-3 and 11 nm-4. These divided electrodes 11 nm-$\alpha$ ($\alpha$=1, 2, 3, 4) are drawn out with the lead wires 12 nm-$\alpha$ and connected to the output ends 13 nm-$\alpha$ of the liquid crystal driving circuit 13. By applying voltage to the electrodes 11 nm-$\alpha$, the light transmitting portion can be changed into light shielding portion.

The signal output from the solid pickup element 4 and amplified by the preamplifier is converted, for example, into 2-bit digital amount $d_1 d_2$ by the A/D converter 108 in accordance with the level, and in the encoder 109 the binary digital amount $d_1 d_2$ is made into the signal of 0 (low level) or 1 (high level) and applied from the 4 outputs to the 4 input terminals for switching of the multiplexer circuit 110.

The digital amount $d_1 d_2$ is converted in the encoder 109, for example, from "00" to "0000", from "01" to "0001", from "10" to "0011" and from "11" to "0111", switched for every 4 units by the multiplexer circuit 110, and input to the liquid crystal driving circuit 13.

The multiplexer circuit consists, for example, of 4 multiplexers arranged in parallel.

Figure 27:
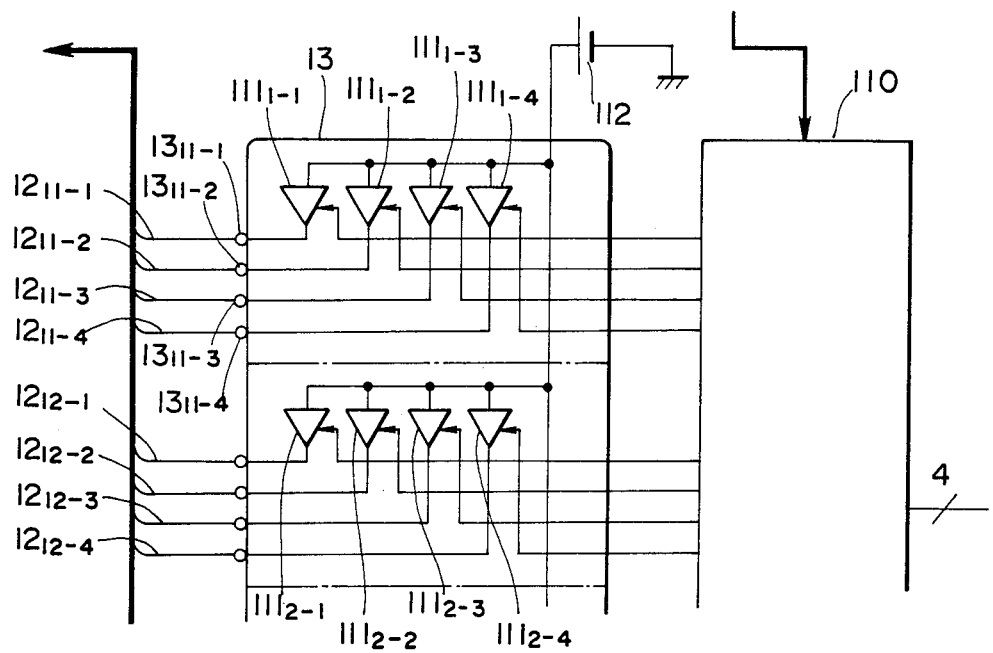

The signal output from the multiplexer circuit 110 is used, for example, as sampling pulse, and if this signal is high level, the level output from the output end 13 nm-$\alpha$ of the hold circuit 111 v-$\alpha$ (v=1, 2, ...; $\alpha$=1, 2, 3, 4), as shown in FIG. 27, is maintained at high level potential of the battery 112. This maintenance is for the time of about 1 frame period to be selected next by the multiplexer circuit 110.

In the multiplexer circuit 110, the output ends of nm set are sequentially switched by means of the switching signals output from the switching circuit 113, synchronized with the clock signal of the driving circuit 58. Here nm (n×m) is number of picture elements, i.e. number of light receiving elements of the solid pickup element 4 or number of blocks in the liquid crystal filter 107. The number of lines of the switching signal provided is the number sufficient to sequentially switch the nm set.

The hold circuit 111 v-$\alpha$, when the sampling pulse to become high level selected by the multiplexer circuit 110 is applied to the control ends, applies the high level signal to the corresponding electrode part of the liquid crystal filter 107 making the part into light shielding portion until the next selection is made by the multiplexer circuit 110, and if the sampling pulse is not applied to the control end (in other words, low level sampling pulse), the low level signal is output regardless of the previous value until the next selection is made by the multiplexer circuit 110, and the electrode portion maintains the light transmitting portion.

That is, the level of the picture element signal output from the light receiving element is A/D-converted, and if the digital amount corresponding to the level is big, the number of high level signal lines output from the 4 output ends of the encoder 109 increases, the voltage of the high level number is applied to each 4 electrode parts of the blocks in the liquid crystal filter 107 on the front side of the corresponding light receiving element which output the picture signal, to maintain the light shielding portion.

That is, the automatic light controlling means to increase the light shielding portion when the quantity of light received is too big and not to shield the light when the quantity of light is too small is formed.

The following will describe the operation of the embodiment 14 of this invention thus made up.

The image of a subject is formed on the image forming face of the solid pickup element 4 by the object lens 3. This image is resolved into picture elements by the light receiving elements, sequentially output as electrical signal (picture element signal) to correspond to the picture element together with the clock signal and displayed in color on the color television receiver 14.

On the other hand, the signal output from the solid pickup element 4 is converted into digital amount by the A/D converter 108 in accordance with the signal level, converted by the encoder 109 into the digital amount which becomes high level by the number corresponding to the digital amount and sequentially input to the multiplexer circuit 110.

The multiplexer circuit 110 is sequentially switched synchronized with the reading of the signal of each light receiving element, for example, if 1st set is selected and, for example, the signal "0001" is output from the encoder 109 side, corresponding to the output signal of the light receiving element of the 1st row and 1st column, the high level sampling pulse is applied only to the hold circuit $111_{1\text{-}4}$ in FIG. 27 and the driving voltage output from the output end $13_{11\text{-}4}$ in the liquid crystal driving circuit 13 is kept at high level and the output level of the output ends $13_{11\text{-}1}$, $13_{11\text{-}2}$ and $13_{11\text{-}3}$ connected to the other hold circuits $11_{11\text{-}1}$, $11_{11\text{-}2}$ and $11_{11\text{-}3}$ is kept at low level.

Therefore, in the block $10_{11}$ of the 1st row and 1st column in the liquid crystal filter 107, the electrode part $11_{11\text{-}4}$ becomes the light shielding portion due to the voltage applied and the remaining maintains the light transmitting proportion. Similarly, in accordance with the signal level of other light receiving elements, the quantity of light received is also controlled for the electrode parts in the blocks 10 of the liquid crystal filter 107 on the front of the light receiving elements.

Since the quantity of light received by each light receiving element is controlled for each frame period and the controlling state is maintained during the period, automatic light control is made to achieve the effective quantity of light for each light receiving element (for each frame period).

Since this invention controls the light shielding area (light transmitting area) of the liquid crystal filter 107 parts covering the corresponding light receiving element in accordance with the level of the signal output from each light receiving element and synchronized with the signal output, for each picture element, as aforementioned, even if the quantity of light incident upon the light receiving elements on the image pickup face corresponding to one picture is locally too big, the blooming phenomenon can be presented from occurring by quickly increasing the light shielding portion at the light transmitting portion in question in accordance with the signal output and during the next frame period, proper brightness (contrast) can be obtained.

Since the quantity of light received can be quickly controlled for each picture element as stated above, this invention can sufficiently cope with even such situation that one picture includes dark part and excessively bright part and if the quantity of incident light is decreased generally through throttling, etc., the dark part becomes difficult to be identified and if not throttled, the blooming is caused due to the bright part. Also, a means to control the quantity of light received is provided, and the dynamic range can be widely expanded. Therefore, even if a solid pickup element 4 with narrow dynamic range is used, the range width can be compressed to pick up the image. In such a case, what was compressed can be returned to the original state on the reproduction side and displayed as required, and truer reproduced image can be obtained.

Figure 28:
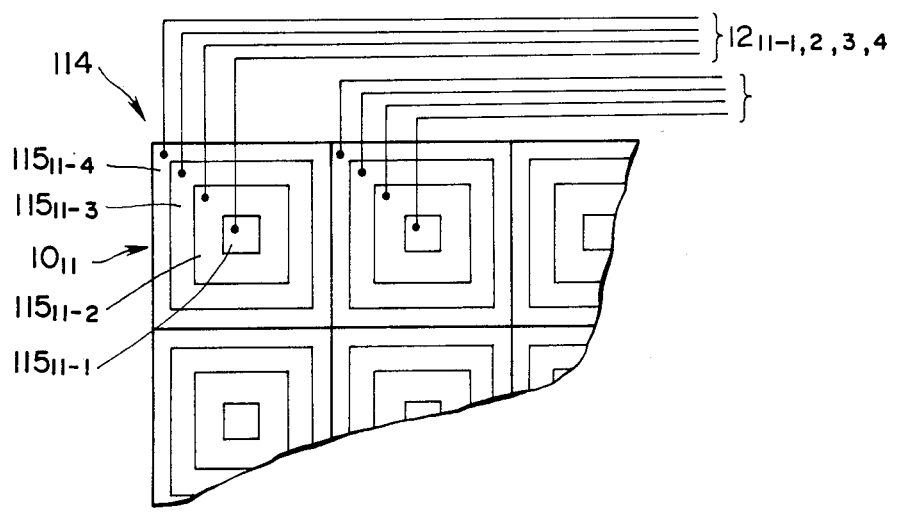

FIG. 28 shows the shape of the electrode part of the liquid crystal filter in the fifthteenth embodiment of this invention.

In the liquid crystal 114 in this embodiment, each block 10nm is formed with a square electrode part 115nm-1 and 115nm-2, 115nm-3 and 115nm-4 arranged in a way to cover the electrode part 115nm-1 sequentially. (n=m=1, i.e. 1st row and 1st column)

When the above liquid crystal filter 114 is used, approximately the same action effect can be obtained.

The invention is not limited to the aforementioned embodiments and, for example, more divided electrode parts can be formed in the block 10nm to cover the picture elements (light receiving elements) in the aforementioned liquid crystal filters 107 and 114 to control the quantity of light received at more detailed level.

The division to form the electrode parts is not limited to equal division and irregular division is also possible and the parts without formation of the electrodes (parts always transmitting light) can also be provided. And the sequence of the light shielding parts can be selected optionally.

In the above embodiments, the control is independently made for each light receiving element to correspond to each picture element, but this invention is not limited to this, and for example, the control can be commonly made for 2 blocks to tens of blocks, i.e. for the connected light receiving element group. In such a case, the number of the lead wires to the electrode parts can be greatly reduced. In such a case each picture element is closely related to the nearest picture element, and therefore, the simplification may make it possible to control the quantity of light in the state similar to the light control for each picture element (or for each light receiving element).

In case the common control is made for several blocks to tens of blocks, those which continue in horizontal or vertical lines may be grouped or the division can be made at a proper scale into square shapes or rectangular shapes and grouped. In such a case, each group of the light receiving elements can represents the signal to be A/D-converted or the signal obtained by adding or integrating the signals of the light receiving elements to form these groups can represent the signal to be A/D-converted.

The above fourteenth and fifthteenth embodiments can be used not only for the ordinary image pickup equipment as described above, but also for image pickup means for observation in an endoscope with a lighting means.

The A/D converter 108 to convert the signal level from the light receiving element into digital amount is not necessarily to be the one with good linearity, and instead of using the A/D converter 108 and encoder 109, multiple comparators with different reference levels set can be provided in parallel and the outputs can be input to the multiplexer 110.

The liquid crystal driving circuit 13 is not limited to the aforementioned makeup and latch, etc. can also be used.

In the above embodiments, the light is shielded at high level, but it is also possible to shield the light at low level.

In the case of the color image pickup in the aforementioned embodiments, the white balance deviation can be prevented by grouping for light control the tri-color picture elements in accordance with the arrangement of the mosaic or other tri-color filters. It is also possible to add the adjacent tri-color picture signals and average them in the integrating circuit before converting into the digital amount.

In the case of the color image pickup, the pickup or reproduction in truer tone of color can be achieved without losing the white balance, by inserting an amplifier for color correction, for example, after the integrating circuit and on the way to the automatic light controlling circuit.

It is clear that the aforementioned fourteenth and fifthteenth embodiments can be used not only for the color image pickup but also black and white image pickup.

FIG. 29 shows an endoscope equipped with the sixteenth Embodiment which can prevent blooming with a simple structure and can obtain the color image with wide dynamic range.

In the endoscope 121, the solid pickup element 4 provided on the end side of the inserting member 2 is for color image pickup which has mosaic or stripe tri-color filter on its image pickup face. On the front of the filter the photochromic glass 122 (enlarged and shown in FIG. 30) is provided.

The photochromic glass is a medium whose light transmission factor changes reversely in accordance with the incident light quantity. That is, this glass 122 shows low transmission factor when the quantity of incident light is big, and increases the transmission factor when the quantity of incident light decreases and this makes it possible to form a means to automatically control the quantity of light incident upon the solid pickup element 4.

The output of the solid pickup element 4 is input divided into R, G and B color signals by the sample hold circuits 123R, 123G and 123B which form the video processor 9 and with the sampling pulse output from the sampling pulse generating circuit 124, and displayed in color on the color television receiver 14.

In the light source unit 125, the member provided before the incident end of the light guide 16 is spectral characteristic correcting filter 126.

When a nearby subject is observed with the endoscope 121 equipped with the sixteenth embodiment thus made up, if the quantity of light incident upon the solid pickup element 4 side via the object lens 3 is too big, the transmission factor of the autochromic glass 122 decreases to decrease the quantity of light to be received by the light receiving element. On the other hand, if the quantity of light incident upon the solid pickup element 4 side via the object lens 3 is too small for such reason that the subject is far away, the transmission factor of the photochromic glass 122 increases.

Therefore, the quantity of the light incident upon the solid pickup element 4 is always automatically controlled to the value suitable for image pickup and reproduction without the operator controlling the intensity of the illuminating light. Therefore, the blooming phenomenon which is caused by excessive quantity of incident light can be prevent and also the image can be taken out as the signal compressed within the saturation level of the solid pickup element 4, i.e. the dynamic range can be expanded. Therefore, it is effective even for the diagnosis of a part whose color changes delicately such as in the initial state of the affected part. Also, it can be easily made up with almost no need of enlarging the shape, only by attach such medium as the photochromic glass 122 to the image pickup face (light receiving face) of the solid pickup element 4. Therefore, it can be contained in the end part of the inserting member of the endoscope whose diameter is required to be small.

The sampling pulse output from the sampling pulse generating circuit 124 is in accordance with the mosaic or stripe arrangement. For the video processor 9, the signal output from the solid pickup element 4 can be passed through an amplifying circuit which shows the input and output characteristics of exponential function and input to the display side by inserting a circuit to correct the signal compressed by the photochromic glass 122.

The above embodiment uses the color pickup element equipped with mosaic filter or stripe filter, but the color image pickup can also be achieved by the color face sequential system lighting using a monochromatic pickup element.

It is clear that many other embodiments can be formed without deviating from the spirit and scope of this invention. This invention is not limited to the particular embodiments except the limitations stated in the claims.

We claim:

1. Automatic dimmer for an endoscope characterized in that it has a long and narrow inserting member having an inserting end at one end and a viewing end at the opposite end, image forming lens system at the inserting end for forming the image of a subject, solid pickup element whose image pickup face is provided at the focal point of the said image forming lens system in said inserting end, a video prooessor at said viewing end of said inserting member for receiving signals corresponding to the picture elements output from said solid pickup element and for outputting said signals as color signals, display equipment for displaying a color picture with said color signals output from said video processor, illuminating means at said inserting end of said inserting member for illuminating within the image forming range of said lens system, said illuminating means including a light distributing lens at the inserting end of said inserting member, a light source for said illuminating means, a light distributing lens, means responsive to applied electric signals for regulating the quantity of light transmitted from said light source to said light distributing lens, dimmer signal generating means responsive to said color signals from said video processor and for forming dimmer signals, and driving circuit means for outputting an electrical signal and for changing the quantity of light from said light source to said illuminating means in accordance with the level of the signal applied.

2. An automatic dimmer for an endoscope as recited in claim 1 further characterized in that said light distribution lens for regulating the light quantity is installed in the light source at the rear end of the light guide inserted in the inserting member.

3. An automatic dimmer for an enoscope as recited in claim 1 further chracterized in that said dimmer signal generating means consists of adder and integrating circuits.

4. An automatic dimmer for an endoscope as recited in claim 1 further characterized in that said dimmer signal generating means consists of adder, integrating and color correction circuits.

5. An automatic dimmer for an endoscope, as recited in claim 1 characterized in that said illuminating means includes two light shileding members of slit type and arranged in reed-screen-like fashion one relative to the other and vibrator means for movng one of said shielding members.

6. An automatic dimmer for an endoscope as recited in claim 5 further characterized in that one of said light shielding members is provided with flyeye lens to condense and increase the quantity of light to pass through the light transmitting part.

7. An automatic dimmer for an endoscope, as recited in claim 1 characterized in that said illuminating means includes a liquid crystal shutter controlled to transmit or shield the light by ON/OFF operation of applied voltage.

8. An automatic dimmer for an endoscope, as recited in claim 7 characterized in that said light distributing lens for regulating the quantity of light includes means for changing the light transmitting area of the liquid crystal shutter.

9. An automatic dimmer for an endoscope as recited in claim 7 further characterized in that said driving circuit means outputs an electrical signal for changing the light transmitting time of the liquid crystal shutter.

10. Automatic dimmer for endoscope characterized in that is has a long and narrow inserting member having an inserting end at one end and viewing end at the opposite end, image forming lens system at the inserting end for forming the image of a subject, solid pickup element whose image pickup face is provided at the focal point of the said image forming lens system in said inserting and, a video processor at said viewing end of inserting member for receiving signals corresponding to the picture elements output from said solid pickup element and for outputtting said signals as color signals, display equipment for displaying a color picture with said color signals output from said video processor, illuminating means for illuminating the subject within the range of image forming of said image forming lens system, said illuminating means including a light distributing lens at the inserting end of said inserting member, a light quantity changing member in the light path between said image forming lens system and the image forming face of said solid pickup element for changing quantity of light incident upon the light receiving elements of said image forming face by application of electric signals, dimmer signal forming means for receiving the color signals output from the aforementioned video processor and forming a dimmer siganls, and a driving circuit for changing the output of the electrical signals to be applied to said light quantity changing member in accordance with the level of the dimmer signal applied.

11. An automatic dimmer for an endoscope as recited in claim 10 further characterized in that said dimmer signal forming means consists of an adder and integrating circuit.

12. An automatic dimmer for an endoscope as recited in claim 10 further characterized in that said dimmer signal forming means consists of adder, integrating and color correction circuits.

13. An automatic dimmer for an endoscope as recited in claim 10 further characterized in that said light quantity changing member includes two light shielding members of slit type light transmitting and light shielding parts arranged in the reed-screen-like fashion, one of said light shielding members being movable relative to the other by vibrator means.

14. An automatic dimmer for an endoscope as recited in claim 13 further characterized in that one of said light shielding members is provided with flyeye lens for condensing and increasing the quantity of light to pass through the light transmitting part.

15. An automatic dimmer for an endoscope as recited in claim 10 further characterized in that said light quantity changing member is a liquid crystal shutter controlled to transmit or shield the light by ON/OFF operation of applied voltage.

16. An automatic dimmer for an endoscope as recited in claim 15 further characterized in that said driving circuit outputs electrical signals for changing the light transmitting area of said liquid crystal shutter.

17. An automatic dimmer for an endoscope as recited in claim 15 further characterized in that said driving circuit outputs electrical signals for changing the light transmitting time of the liquid crystal shutter.

18. Automatic dimmer for an endoscope characterized in that is has a cylinder with one end opened, image forming lens system provided in said cylinder to form the image of a subject, solid pickup element having an image forming face at the focal point of said image-forming lens system, video processor for receiving the signal output from said solid pickup element and outputting said signal as color signals, display equipment for displaying a color picture from said color signals from said video processor, light illuminating means for illuminating said subject, said image forming face of said solid pickup element having a plurality of light receiving elements; means on each said light receiving elements for generating and outputting a signal in proportion to the illuminating light received thereby, a liquid crystal filter in the light path of illuminating light from said subject to said light receiving elements of said image forming face for dividing said image forming face into signal producing areas, and means for changing and controlling the light transmitting area of said liquid crystal to provide a shutter on the light receiving side of the light receiving elements in proportion to the level of the signal output from each light receiving element.

19. Automatic dimmer for endoscope characterized in that it has a long and narrow inserting member at one of its ends and viewing means at its opposite end, an image forming lens system at the end side of the inserting member to form an image of a subject, a video pickup element having an image pickup face at the focal point of said image forming lens system, a video processor at the opposite viewing means end of said endoscope for receiving signals from said video pickup element and for outputting said signals as video color signals, display equipment for displaying a color picture from the color signals output from said video processor, light illuminating means having light distributing lenses for illuminating the subject within the range of image forming lens system at said end side of said inserting member, and photochromic glass at the image forming face of said video pickup element for transmitting a smaller quantity of light, as the quantity of incident light transmitted to said pickup increases.

20. An automatic dimmer for an endoscope as recited in claim 19 further characterized in that said video processor includes an amplifying circuit with exponential function input/output characteristic for correcting the light transmission characteristic of said photochromic glass.

* * * * *